United States Patent [19]
Lippitt et al.

[11] Patent Number: 5,924,175
[45] Date of Patent: Jul. 20, 1999

[54] ANNULARLY EXPANDING AND RETRACTING GRIPPING AND RELEASING MECHANISM

[76] Inventors: Robert G. Lippitt, 515 Rosewood Dr., Smithfield, N.C. 27577; Raymond F. Lippitt, 8601 Burning Tree Rd., Bethesda, Md. 20817

[21] Appl. No.: 09/069,160

[22] Filed: Apr. 29, 1998

Related U.S. Application Data

[60] Provisional application No. 60/045,068, Apr. 29, 1997, provisional application No. 60/056,527, Aug. 21, 1997, provisional application No. 60/045,322, May 1, 1997, and provisional application No. 60/056,509, Aug. 21, 1997.

[51] Int. Cl.⁶ .......................... A61B 17/22; A61B 17/50
[52] U.S. Cl. .......................... 24/537; 606/127; 294/19.2
[58] Field of Search .................. 24/537, 536, 535, 24/530; 606/113, 127; 56/333; 294/19.2; 81/53.1, 53.11

[56] References Cited

U.S. PATENT DOCUMENTS

| | | | |
|---|---|---|---|
| 1,723,091 | 8/1929 | St. John | 294/19.2 |
| 2,549,257 | 4/1951 | Staunt | 294/19.2 |
| 2,990,668 | 7/1961 | Brendel | 56/333 |
| 3,472,230 | 10/1969 | Fogarty | 606/127 |
| 4,471,777 | 9/1984 | McCorkle, Jr. | |
| 4,807,626 | 2/1989 | McGrirr | 606/127 |
| 4,997,435 | 3/1991 | Demeter | 606/127 |
| 5,190,557 | 3/1993 | Borodulin | 606/127 |
| 5,312,417 | 5/1994 | Wilk | 606/127 X |
| 5,417,697 | 5/1995 | Wilk et al. | 606/113 |
| 5,496,330 | 3/1996 | Bates et al. | 606/127 |

FOREIGN PATENT DOCUMENTS

| | | |
|---|---|---|
| 0 769 305 | 4/1997 | European Pat. Off. . |
| 29 45 237 | 5/1981 | Germany . |
| 37 17 657 | 12/1988 | Germany . |
| WO 94 06357 | 3/1994 | WIPO . |

*Primary Examiner*—James R. Brittain
*Assistant Examiner*—Robert J. Sandy

[57] ABSTRACT

An annularly expanding and retracting gripping and releasing mechanism comprises an annular array of longitudinally fixed flexure elements and a corresponding number of longitudinally movable flexure elements. The arrangement is such that a longitudinally outward movement of the longitudinally movable flexure elements within the annular array of longitudinally fixed tubular flexure elements causes the fixed flexure elements to flex transversely outwardly and creates an annularly expanded condition defined by an annular series of transversely outwardly flexed fixed flexure elements interconnected at their flexure points by an annular series of arcuately outwardly flexed portions of the movable flexure elements. A manual movement in the opposite direction effects a longitudinally inward movement of the movable flexure elements to cause the expanded condition to progressively retract during which the outwardly flexed fixed flexure elements are progressively less flexed transversely outwardly and the arcuately flexed portions of the movable flexure elements have a progressively less arcuate extent.

13 Claims, 9 Drawing Sheets

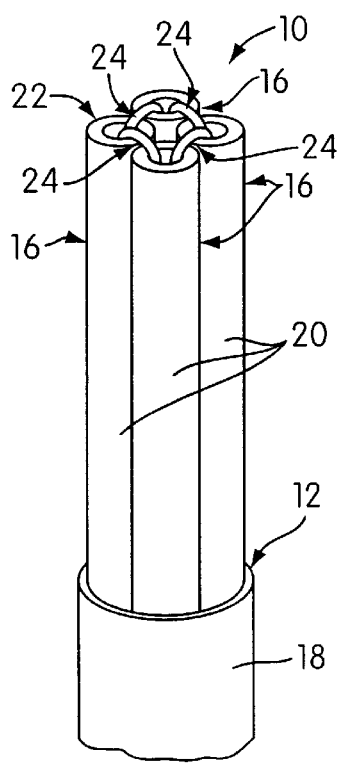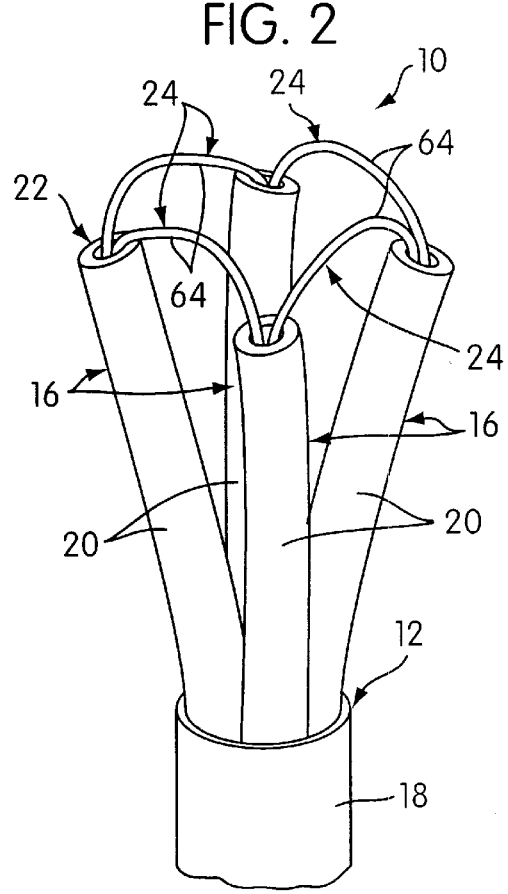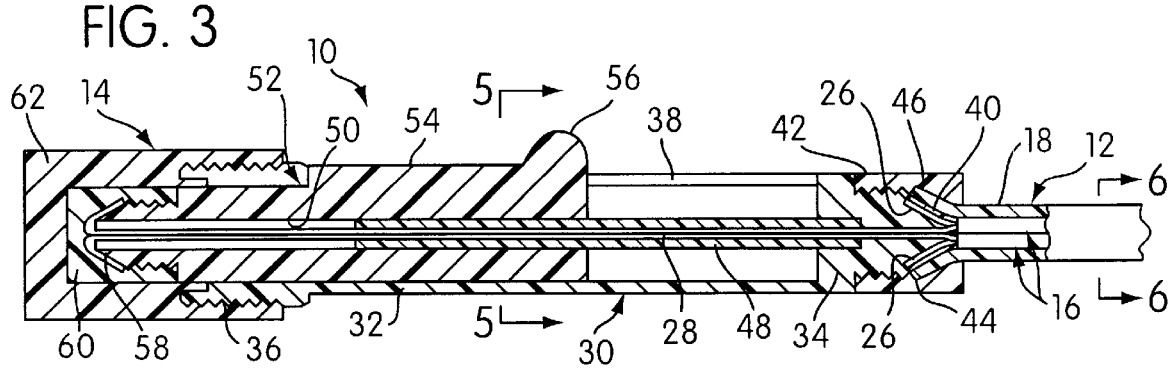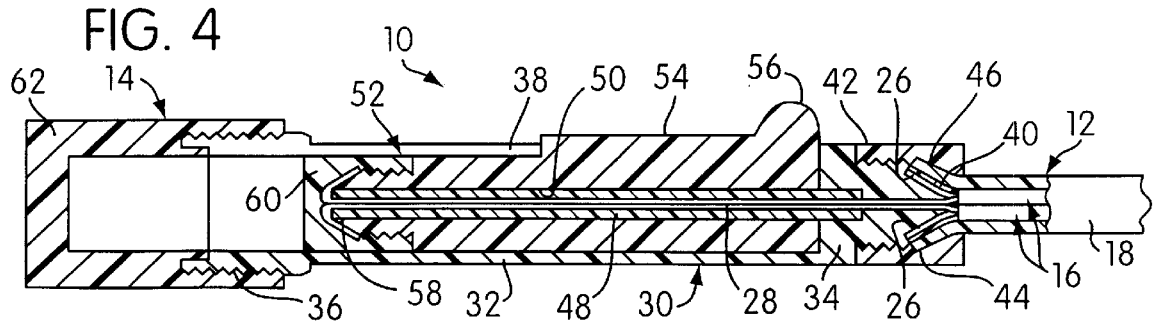

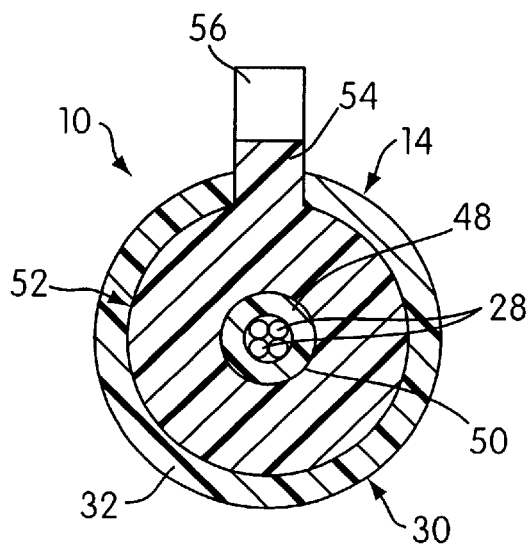
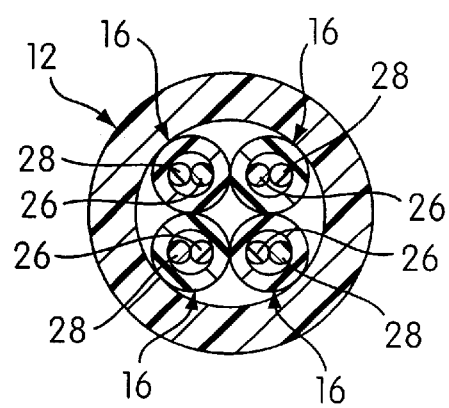
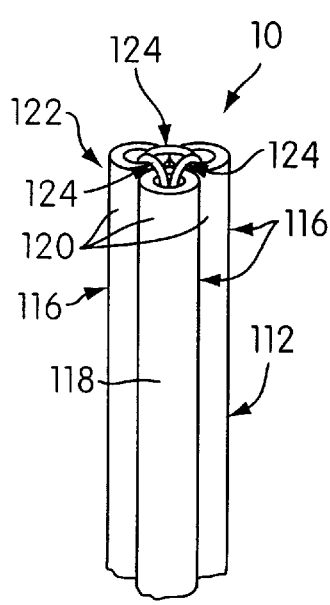
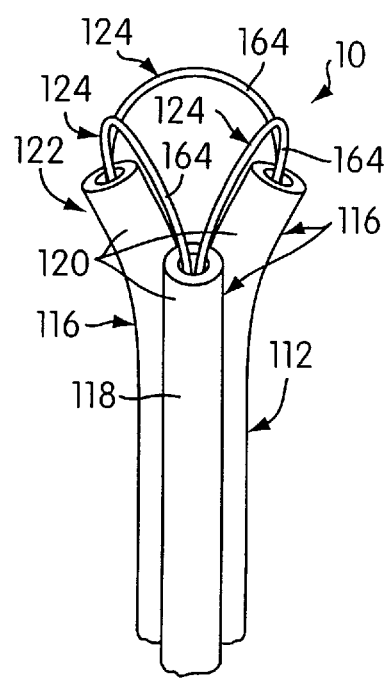
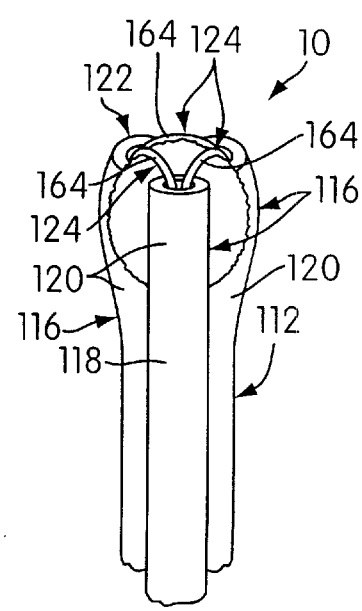

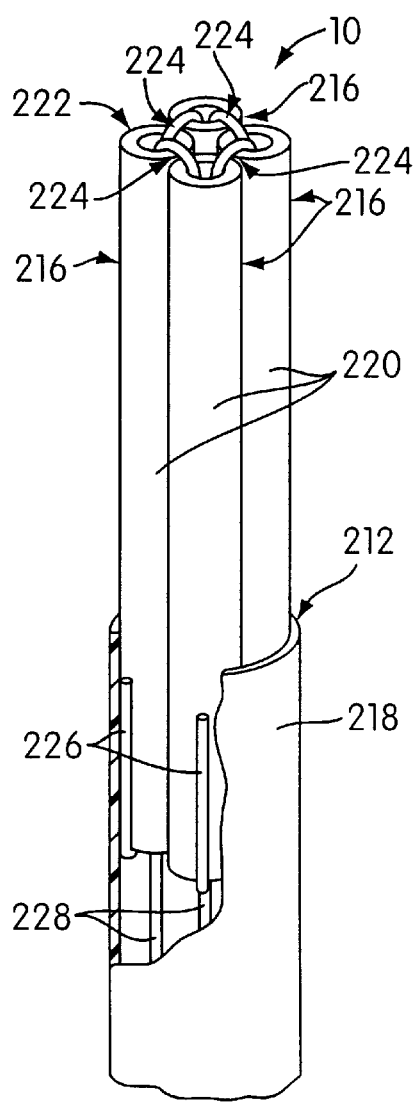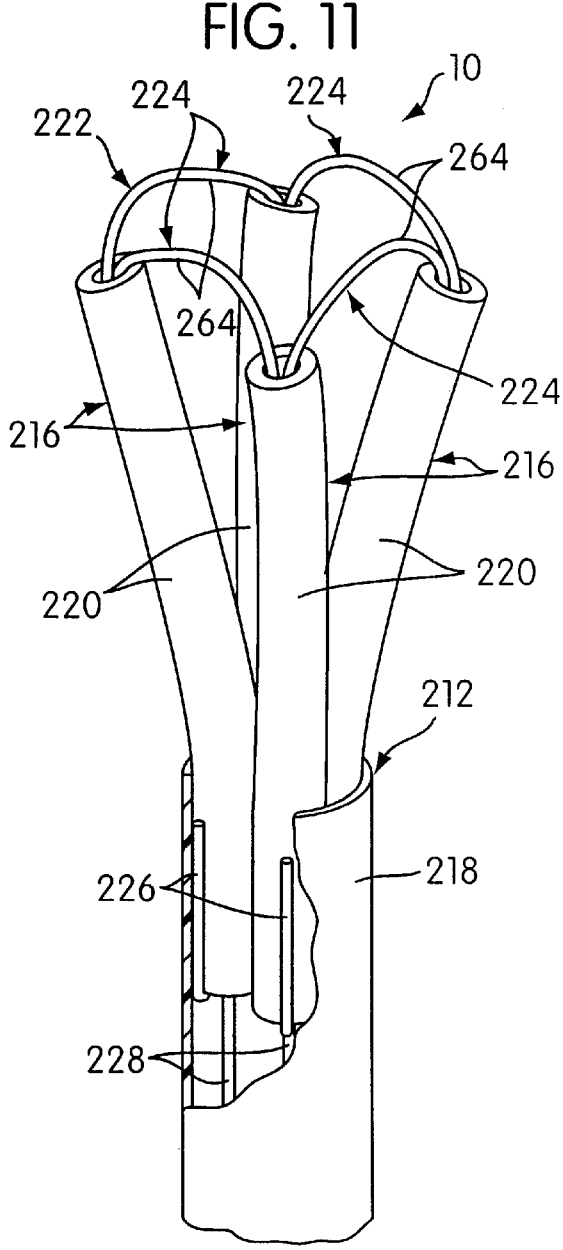

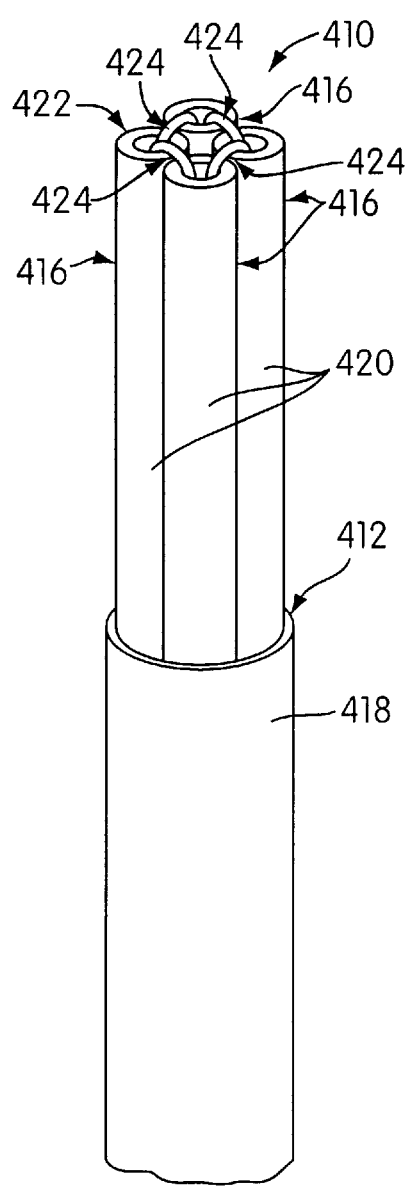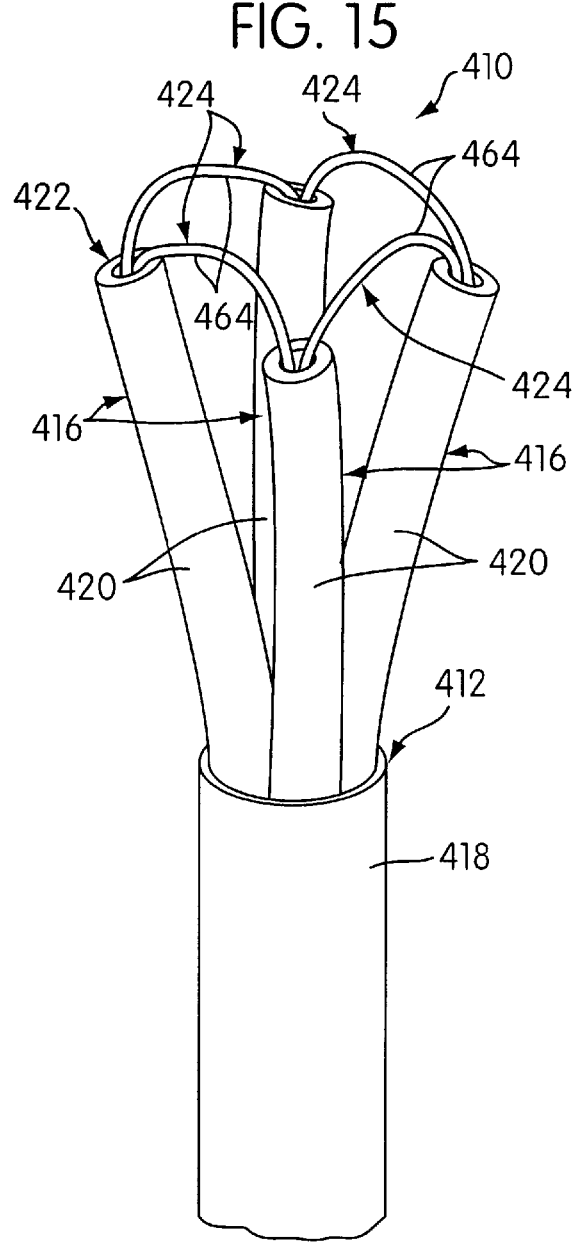

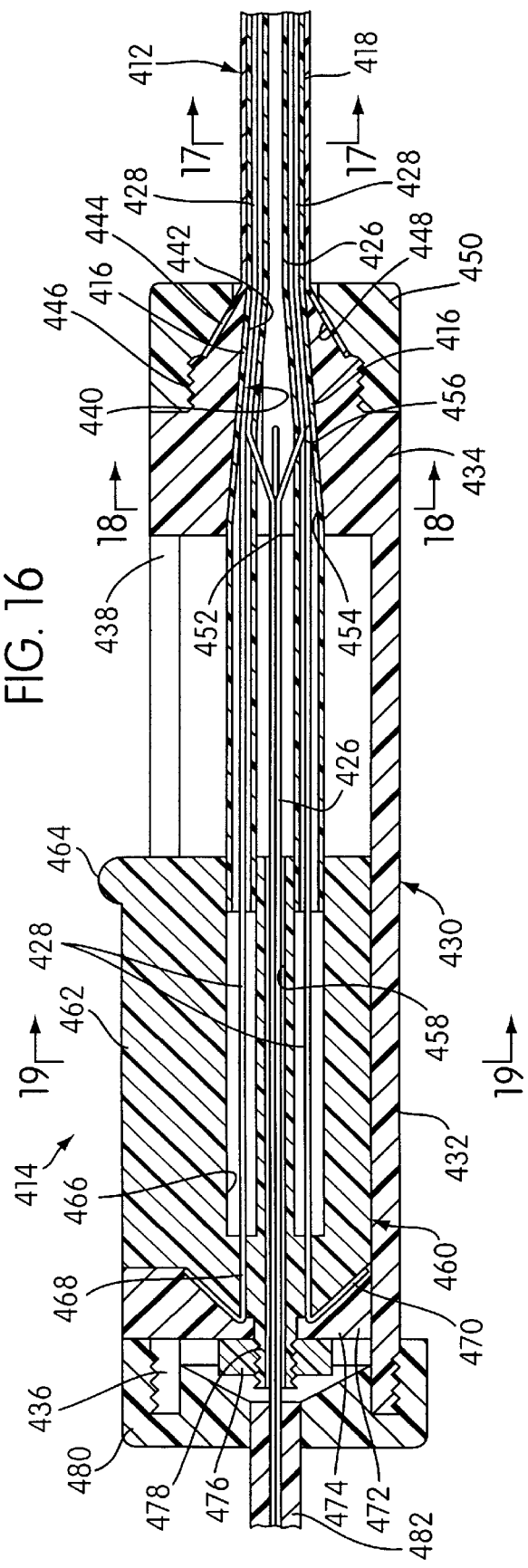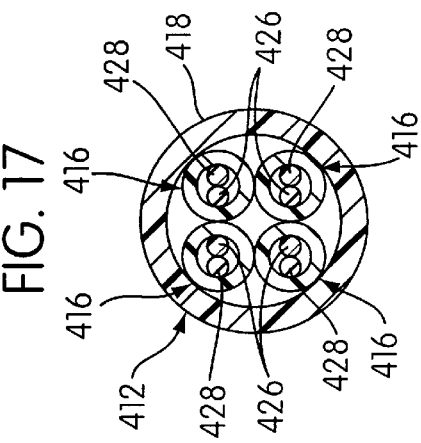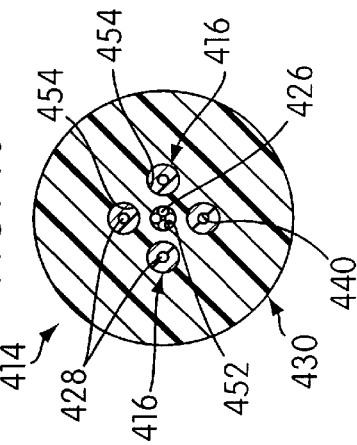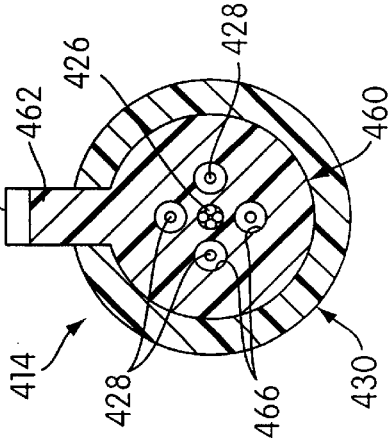

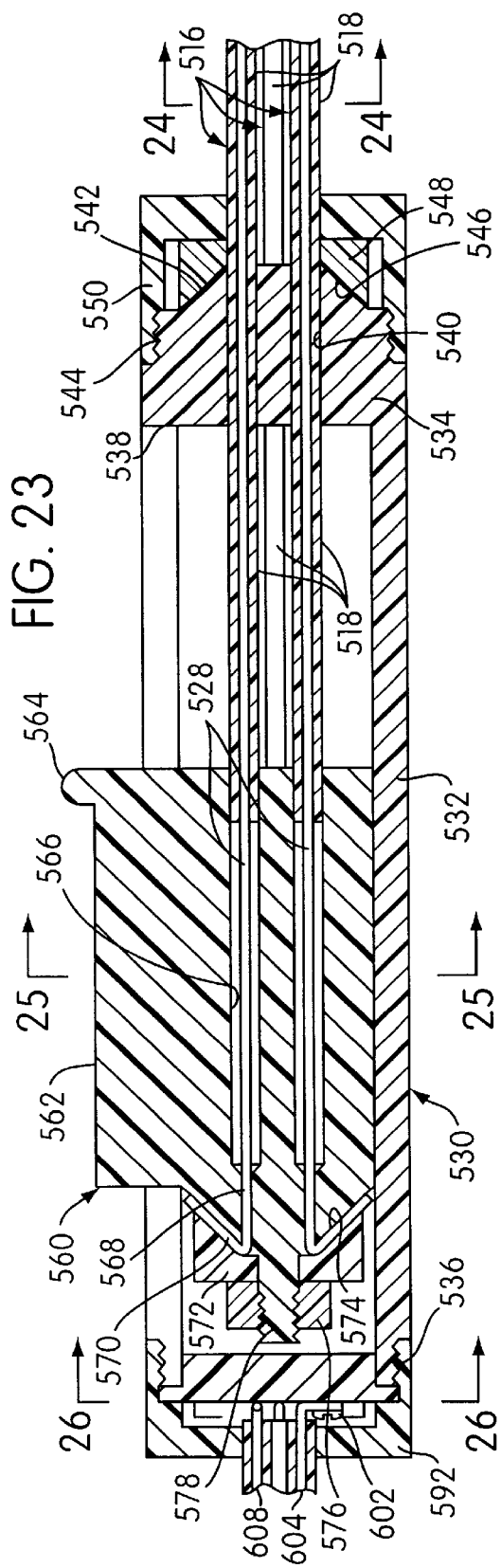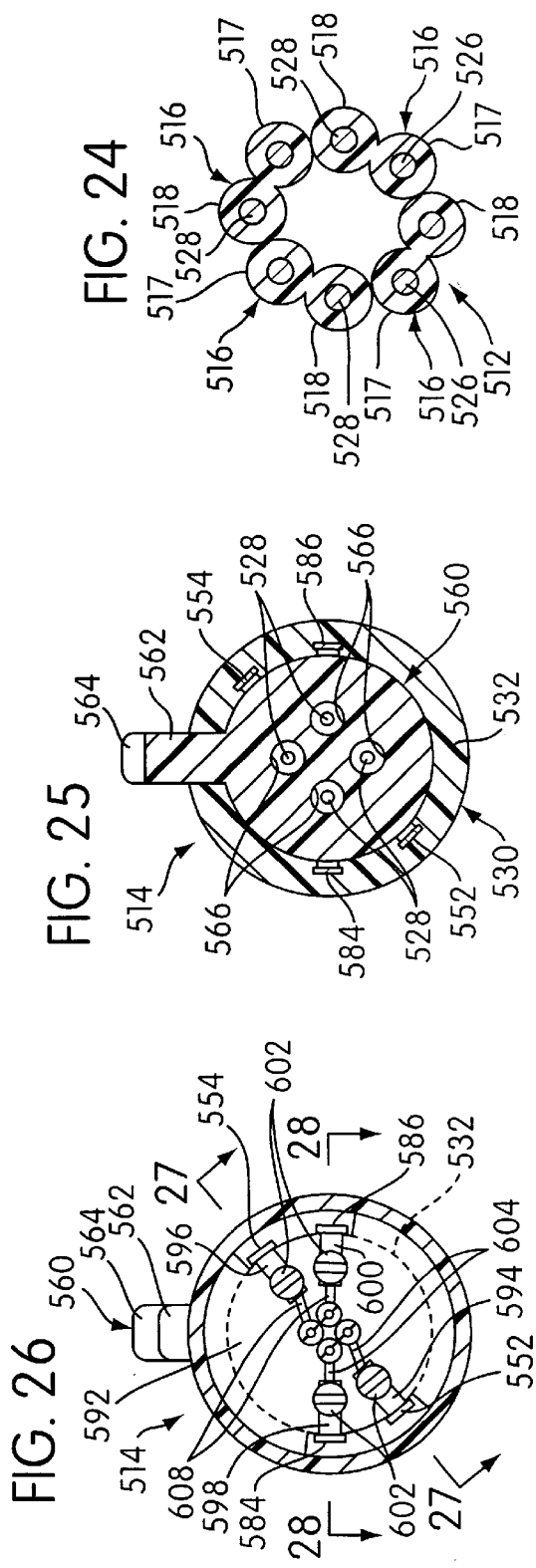

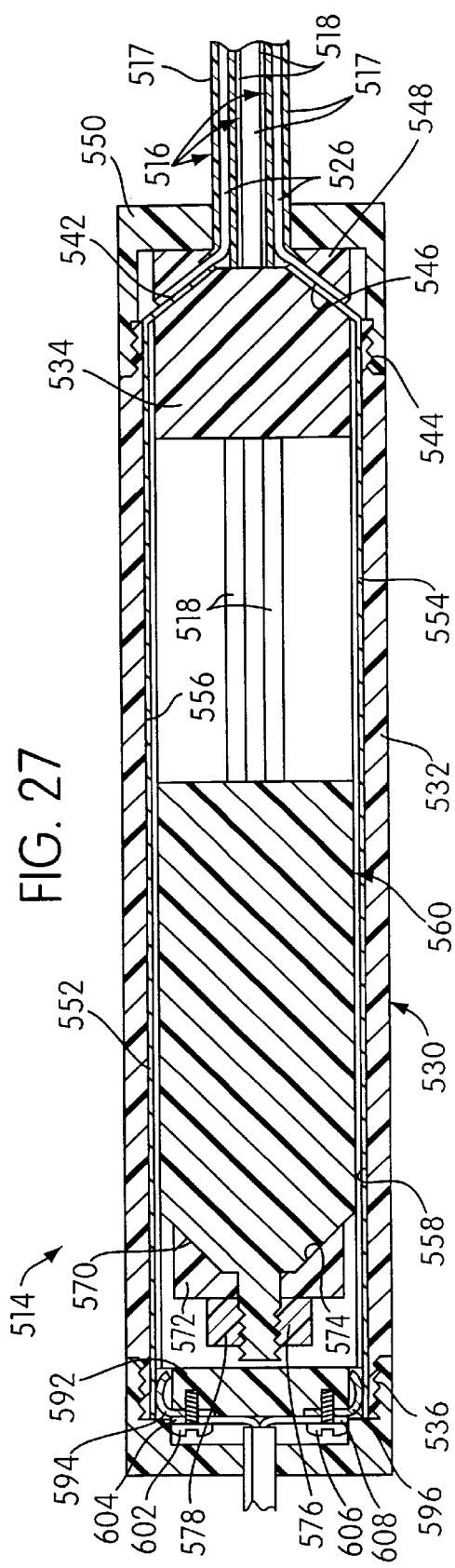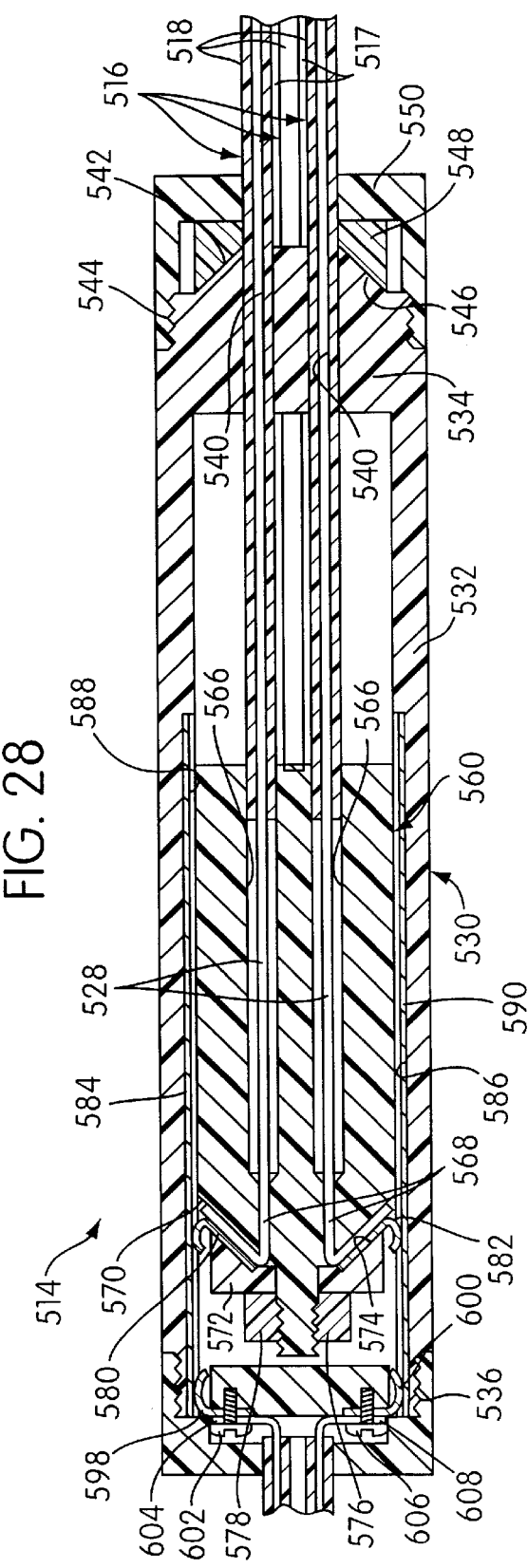

5,924,175

ANNULARLY EXPANDING AND RETRACTING GRIPPING AND RELEASING MECHANISM

This application claims the benefit of U.S. provisional application No. 60/045,068, filed Apr. 29, 1997, U.S. provisional application No. 60/045,322, filed May 1, 1997; U.S. provisional application No. 60/056,527, filed Aug. 21, 1997, and U.S. provisional application No. 60/056,509, filed Aug. 21, 1997.

This invention relates to mechanisms suitable for gripping and releasing objects and more particularly to mechanisms of this type which are constructed and arranged to expand and retract annularly.

Typical mechanisms for gripping and releasing objects provide a pair of opposed jaws capable of being moved toward and away from one another. In the medical field, a good example of a mechanism of this type is the so-called alligator clamp. In many cases, it is more desirable to include more than two gripping elements arranged annularly in order to surround the object at three or more annular positions prior to gripping. Examples of mechanisms of this type are found in the well-known mechanisms used in coin-operated prize-hoisting machines found in arcades, which include three or four rigid object-engaging elements. There is always a need for a new mechanism of this type particularly one which is capable of active positive expansion and retraction. In terms of usage, it would be desirable for the mechanism to be capable of miniaturization so as to be remotely actuatable at the end of a canula for medical usage in retrieving objects, such as kidney stones and the like, from human beings.

It is an object of the present invention to fulfill the need expressed above. In accordance with the principles of the present invention, this objective is achieved by providing an annularly expanding and retracting gripping and releasing mechanism comprising an annular series of longitudinally fixed flexure elements and a corresponding series of longitudinally movable flexure elements. The fixed flexure elements are fixed relatively together in annular array at a confining fixed position and have a flexure position spaced longitudinally outwardly therefrom. Each of the fixed flexure elements is constructed and arranged to flex at the flexure position thereof transversely outwardly and inwardly about the confined fixed position thereof. Each of the movable flexure elements has an end fixed with respect to the flexure position of one of the fixed flexure elements and extends therefrom in longitudinally movable and generally transversely confined relation to a receiving portion of an adjacent fixed flexure element the outer end of which is adjacent the flexure position thereof. The movable flexure elements are constructed and arranged to be moved longitudinally in an outward direction with respect to the receiving portions associated therewith to extend in an arcuately flexed condition generally beyond the flexure positions of the fixed flexure elements to cause the latter to flex transversely outwardly and create an expanded condition defined by an annular series of transversely outwardly flexed fixed flexure elements interconnected by an annular series of arcuately flexed portions of the movable flexure elements. The movable flexure elements are constructed and arranged to be moved, when in the expanded condition thereof in a direction inwardly with respect to the receiving portions associated therewith to cause the expanded condition to be progressively retracted during which the annular series of transversely outwardly flexed fixed flexure elements are progressively less flexed transversely outwardly and the annular series of arcuately flexed portions of the movable flexure elements have a progressively less arcuate extent.

These and other objects of the present invention will become more apparent during the course of the following detailed description and appended claims. The invention may best be understood with reference to the accompanying drawings wherein an illustrative embodiment is shown.

DESCRIPTION OF THE DRAWINGS

FIG. 1 is a perspective view of the distal end portion of a canula assembly of a medical extractor showing a gripping and releasing mechanism embodying the principles of the present invention in a retracted insertion position;

FIG. 2 is a view similar to FIG. 1, showing the gripping and releasing retrieving mechanism of the extractor in an expanded maximum deployed position;

FIG. 3 is a sectional view of the proximal end portion of the canula assembly connected with a moving assembly of the extractor of FIG. 1, showing the components in an insertion position;

FIG. 4 is a view similar to FIG. 3 showing the components in a maximum deployed position;

FIG. 5 is an enlarged sectional view taken along the line 5—5 of FIG. 3;

FIG. 6 is an enlarged sectional view taken along the line 6—6 of FIG. 3;

FIG. 7 is a perspective view of the distal end portion of another embodiment of a canula assembly of a medical extractor showing the gripping and releasing mechanism embodying the principles of the present invention in a retracted insertion position;

FIG. 8 is a view similar to FIG. 7, showing the gripping and releasing mechanism in an expanded maximum deployed position;

FIG. 9 is a view similar to FIG. 7, showing the gripping and releasing mechanism in a gripping position with an object;

FIG. 10 is a view similar to FIG. 1 of the distal end portion of another embodiment of a canula assembly of a medical extractor showing another gripping and releasing mechanism embodying the principles of the present invention in a retracted insertion position;

FIG. 11 is a view similar to FIG. 10 showing the gripping and releasing mechanism in an expanded maximum deployed position;

FIG. 14 is a perspective view of an annularly expanding and retracting gripping and releasing mechanism constructed in accordance with the principles of the present invention embodied in the distal end portion of a canula assembly of a medical coagulating, cutting and extracting device, showing the gripping and releasing mechanism in a retracted insertion position;

FIG. 15 is a view similar to FIG. 14, showing the gripping and releasing mechanism in an expanded deployed position;

FIG. 16 is a sectional view of the proximal end portion of the canula assembly connected with a moving assembly of the medical device of FIG. 14, showing the components in an insertion position;

FIG. 17 is an enlarged sectional view taken along the line 17—17 of FIG. 16;

FIG. 18 is a sectional view taken along the line 18—18 of FIG. 16;

FIG. 19 is a sectional view taken along the line 19—19 of FIG. 16;

FIG. 23 is a view similar to FIG. 16, showing another embodiment of a moving assembly used with the gripping and releasing mechanism of FIG. 20;

FIG. 24 is a sectional view taken along the line 24—24 of FIG. 23;

FIG. 25 is a sectional view taken along the line 26—26 of FIG. 23;

FIG. 26 is a sectional view taken along the line 26—26 of FIG. 23;

FIG. 27 is a sectional view taken along the line 27—27 of FIG. 26; and

FIG. 28 is a sectional view taken along the line 28—28 of FIG. 26.

DETAILED DESCRIPTION OF THE PREFERRED EMBODIMENTS OF THE INVENTION

Figure 12:
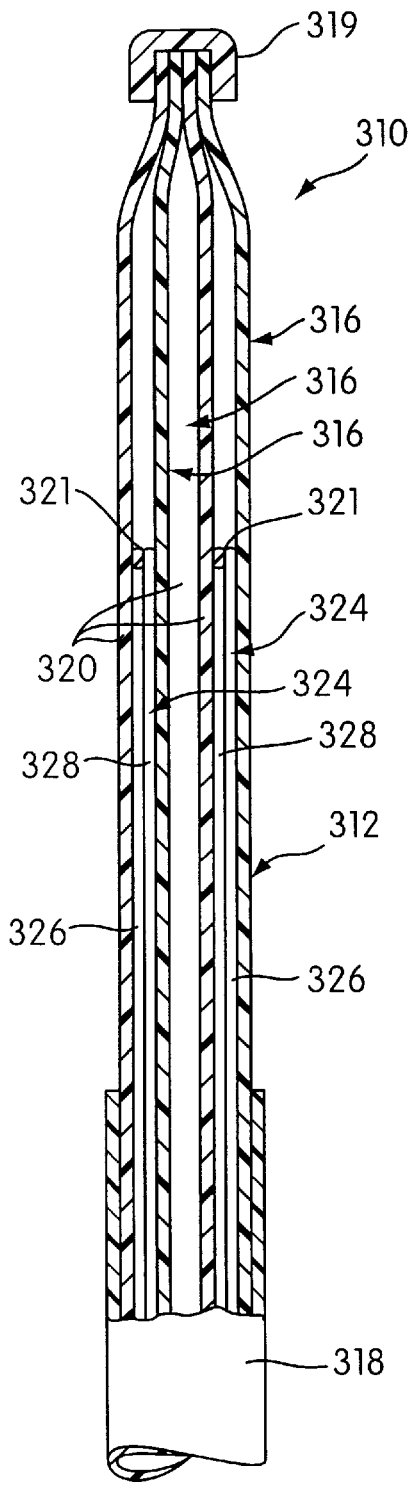
FIG. 12 is a longitudinal sectional view of an annularly expanding and retracting gripping and releasing mechanism embodying the principles of the present invention as used on a distal end portion of a canula assembly of a medical extractor showing the gripping and releasing mechanism in a retracted insertion position.

Referring now more particularly to FIGS. 1–6 of the drawings, there is shown therein one embodiment of an annularly expanding and retracting gripping and releasing mechanism, generally indicated at 22, constructed in accordance with the principles of the present invention embodied in a medical extractor, generally indicated at 10. The extractor shown is particularly constructed to be used in a percutaneous kidney stone extraction procedure. The medical extractor 10 includes, in general, an elongated canula assembly, generally indicated at 12, and a moving assembly, generally indicated at 14, operatively connected with the proximal end portion of the canula assembly 12. The gripping and releasing mechanism 22 of the present invention is formed as the distal end portion of the canula assembly 12.

The canula assembly 12 is essentially constructed as an elongated wall structure providing a generally smooth exterior periphery and a hollow interior. In the embodiment shown, the elongated wall structure is formed by four coextensive side-by-side flexible tubular members, generally indicated at 16. The tubular members 16 are formed of a suitable plastic material such as polyethylene, polypropylene, polyester, polyvinyl chloride, polyimide or the like. For the percutaneous application shown, the four tubular members 16 are encased within a thin walled outer tubular member 18. The outer tubular member 18 is preferably relatively flexible and is formed of a suitable relatively flexible plastic material although a rigid metal material can be utilized if desired.

At the distal end of the canula assembly 12, the flexible tubular members 16 extend outwardly of the distal end of the outer tubular member 18. The outwardly extending distal end sections of the flexible tubular members 16 constitute longitudinally fixed flexure elements 20 forming a part of the annularly expanding and retracting gripping and releasing mechanism, generally indicated at 22 at the distal end of the canula assembly 12.

The canula assembly 12 also includes four wires or rodular members, generally indicated at 24. The wires 24 are preferably made of stainless steel, although other materials both electrically conducting and otherwise may be used. Each wire 24 has a length in excess of twice the length of the flexible tubular members 16. As shown, each wire 24 is bent at a midportion thereof so as to define a fixed wire section 26 and a movable wire section 28.

The four fixed wire sections 26 extend within the four flexible tubular members 16 with the bend being disposed in a flexure position on the longitudinally fixed flexure elements 20 which, as shown, is at the distal free ends of the tubular members 16. The four fixed wire sections 26 are fixed with respect to the four tubular members 16 within which they extend in a manner hereinafter to be more fully explained.

The four movable wire sections 28 also extend within the four tubular members 16, however, not within the same tubular members 16 as the fixed sections 26; but, instead, in adjacent tubular members 16. Each movable wire section 28 extends from the bend which connects it to the associated fixed wire section 26 through its associated tubular member 16 and outwardly beyond the proximal end thereof.

The preferred embodiment of the moving assembly 14 shown in FIGS. 3–5 includes a main body, generally indicated at 30, molded of a suitable plastic or metal material. The main body 30 is of generally tubular construction and of a size to be conveniently gripped in one hand. The main body 30 is formed of a peripheral wall 32 having an end wall 34 at a forward end thereof. The rearward end of the peripheral wall 32 is enlarged and exteriorly threaded, as indicated at 36. An elongated slot 38 is formed in the peripheral wall 32 which extends rearwardly from the forward end wall 34 thereof, completely through the enlarged rear end thereof.

The forward end wall 34 is centrally apertured to receive therethrough the end portions of the movable wire sections 28 which extend beyond the normal ends of the flexible tubular members 16. The forward end wall 34 has its forward extremity shaped into a frusto-conical exterior surface 40 and an intermediate portion is formed with exterior threads as indicated at 42. The exterior frusto-conical surface 40 is sized to cooperate with an interior frusto-conical surface 44 formed on a mounting element, generally indicated at 46, in the form of an interiorly threaded cap. The cap mounting element 46 is centrally apertured to receive therethrough the outer tubular member 18 so as to be capable of being initially moved over the proximal end of the outer tubular member 18. The cap mounting element 46 when threaded on the threads 42 of the end wall 34 serves to secure the proximal ends of the fixed wire sections 26, the proximal ends of the tubular members 16 and the proximal end of the outer tubular member 18 to the main body 30 of the moving assembly 14.

It will be understood, that the securement can be effected by splitting the proximal end of each tubular member 16 and spreading the split end over the exterior frusto-conical surface 40 so that the contained end of the fixed wire section 26 also engages the exterior frusto-conical surface 40 and thereafter spreading a split proximal end of the outer tubular member over the spread out inner tubular member split ends. As the cup mounting element 14 is thereafter turned on the threads 42, the interior frusto-conical surface 44 of the cap mounting element 46, the proximal ends of the wire sections 26 and inner tubular members 16 in engagement with the exterior frusto-conical surface 40 and the proximal end of the outer tubular member 18 in engagement with the interior frusto-conical surface 44 will be squeezed between the exterior and interior frusto-conical surfaces 40 and 46 until all ends are securely held therebetween.

The ends of the movable wire sections 28 which extend beyond the proximal ends of the inner tubular members 16 pass through the central aperture in the end wall 34 and then extend through a small thin walled tube 48 fixed at its forward end within the end wall 34 in alignment with the central aperture of the end wall 34. The tube could be molded integral with the main body 30 although a separate fixed tube is preferred because of its thin wall construction. The thin walled tube 48 extends within a cylindrical through bore 50 formed centrally within a moving member, generally indicated at 52.

The moving member 52 has its exterior shaped into a generally cylindrical configuration so as to slidably engage within the interior of the peripheral wall 32 as the bore 50 slidably engages the exterior of the thin walled tube 48. The moving member 52 moves in opposite longitudinal directions between an insertion position, as shown in FIG. 4 and a maximum deployed position, as shown in FIG. 5. The moving member 52 includes an upstanding digitally engageable portion 54 which extends upwardly through the slot 38 in the main body 30. The digitally engageable portion 54 includes a projection 56 at its forward end for facilitating the digital movement of the movable member 52 in both longitudinal directions with respect to the main body 30.

The rear end portion of the moving member 52 is formed with a frusto-conical exterior surface 58 over which the terminal ends of the movable wire sections 28 are bent when the movable member 52 is disposed in its insertion position. A mounting element 60 in the form of a threaded cap with an interior frusto-conical surface, similar to the cap moving element 46, is threadedly engaged on the end of the moving member 52 to securely fix the movable wire sections 28 thereto.

An end cap 62 is threadedly mounted on the threads 36 at the rear end of the main body 30. The end cap 62 includes a forwardly extending inner annular portion which enters within an interior groove in the rear end of the peripheral wall 32 to maintain the diametrical integrity of the peripheral wall 32. The end cap 62 is constructed so as to permit cap mounting member 60 to freely enter therein with no air lock action; as, for example, by including an oversize bore. It will be understood that the end cap could be centrally apertured or provided with one or more longitudinal grooves in its bore, if made full size, to accomplish the same function.

In the use of the medical extractor 10 in a percutaneous kidney stone removal procedure, the standard preparatory procedures and standard auxiliary equipment are used. Initially, a suitable percutaneous tract to the kidney in the patient's body is provided and an adequate visualization of the collecting system of the kidney by means of a scope is established through the percutaneous track. Next, the distal end portion of the canula assembly 12 is advanced through the scope with the moving member 52 and the gripping and releasing mechanism 22 of the present invention both in the retracted insertion position, as shown in FIGS. 4 and 1 respectively. The advance is continued until the distal end of the canula assembly 12 reaches the targeted area where the stone is to be removed. This advance is accomplished manually feeding the canula assembly 12 through the working channel in the scope. As soon as the distal end of the canula assembly 12 reaches the desired area as determined by visual inspection of the scope, the operator grasps the exterior of the main body 30 of the moving assembly 14 and moves his thumb forward on the digitally engageable portion 54 so as to move the moving member 52 away from the insertion position thereof, shown in FIG. 3, toward the maximum deployed position thereof, shown in FIG. 4. The extent of the forward movement is sufficient to expand the gripping and releasing mechanism 22 to engage the stone to be extracted.

As the moving member 52 is moved forward, the proximal ends of the movable wire sections 28 are moved therewith. Since the movable wire sections 28 are captured peripherally throughout their extent, the movement of their proximal ends with the moving member 52 causes their opposite distal ends to move outwardly of the distal ends of the flexible tubular members 16 or the fixed flexure elements 20. Since the distal ends of the movable wire sections 28 are fixed to the adjacent fixed flexure elements 20 by virtue of the fixture of the integral fixed wire section 26 therewith, the movement of the distal end portions of the movable wire sections 28 outwardly of the fixed flexure elements 20 which contain them causes the fixed flexure elements 20 to be flexed radially outwardly at their free ends and the outwardly extending end portions of the movable wire sections 28 to flex arcuately outwardly beyond the distal free ends of the fixed flexure elements 20.

When the moving member 52 reaches the deployed position, as shown in FIG. 4, the outwardly extending distal end portions of the movable wire sections 28, which constitute longitudinally movable flexure elements 64, are in arcuate configurations outwardly of the flexure positions of the fixed flexure elements 20, as shown in FIG. 2. It can be seen that the flexure position of each fixed flexure element 20 is biased outwardly by two associated movable flexure elements 64, one of which is integrally connected with the fixed wire section 26 therein and one of which is integral with the movable wire section 28 therein. Since the two movable flexure elements 64 associated with each fixed flexure element 20 have their opposite ends associated with the two adjacent fixed flexure elements 20, the flexural movement is imposed symmetrically upon each fixed flexure element 20 by the associated movable flexure elements 64. The result is that the gripping and releasing mechanism 22 expands annularly from its retracted insertion position, as shown in FIG. 1, both radially outwardly and longitudinally outwardly. In its maximum expanded deployed position, as shown in FIG. 2, the extracting mechanism 22 is defined at its outer portion by four longitudinally outwardly arcuately flexed movable flexure elements 64 extending in an open annular series or array. In the embodiment shown, the movable flexure elements 64 are in the form of wire sections 64 constituting distal sections of the movable wire sections 28, the remaining sections of which form continuing sections of the wire sections 64. The inner portion of the maximally expanded deployed gripping and releasing mechanism 22 is defined by four radially outwardly flexed fixed flexure elements 20 extending from a position of confinement determined by the position of the distal free end of the outer tubular member 18.

The deployment configuration whether maximal or less enables the operator to move the expanded gripping and releasing mechanism 22 longitudinally over the targeted kidney stone until it is captured therein. This longitudinal forward movement is a more natural movement to effect capture of the stone in the kidney's collecting system as compared with a lateral movement. Nevertheless, alternatively, it is possible to loop the most convenient arcuate flexure element 64 over the stone to position it inside the deployed gripping and releasing mechanism 22. During the looping movement, it is noted that the fixed flexure elements 20 which are not associated with the movable flexure element 64 used to loop the stone as well as the three movable flexure elements 64 associated therewith provide structure to engage the stone as the looping movement progresses, thus establishing the full entry of the stone within the extracting mechanism 22. The deployment movement is determined to take place in a coordinated relation with the position of the stone within the kidney collecting system. The advancing longitudinal movement or the looping movement can be a coordinated part of the deployment movement or fully sequential. In this way, either the annular series of outwardly arcuately flexed movable flexure elements 64 are moved around the stone or the selected movable flexure element 64 more or less is reached out and looped over the stone. In this coordinated movement, it is noted that there are no sharp points ever presented to deal with which might start hemorrhaging.

Once the stone is positioned within the expanded gripping and releasing mechanism 22, the operator simply moves the moving member 52 of the moving mechanism 14 rearwardly away from the deployed position toward the insertion position shown in FIG. 3. This rearward movement of the moving member 52 effectively retracts the movable flexure elements 64 back into the fixed flexure elements 20 of the retrieving mechanism 22. As this movement progresses, the arcuate extent of the movable flexure elements 64 becomes smaller and the flexure positions at the free ends of the fixed flexure elements 20 move radially inwardly. This progressive movement has the effect of engaging the stone within the four fixed flexure elements 20. As the movable flexure elements 64 continue to move within the fixed flexure elements 20, the outer portion of the gripping and releasing mechanism 22 is retracted both radially and longitudinally inwardly. The retracting outer portion of the gripping and releasing mechanism 22 including the movable flexure elements 64 and free ends of the fixed flexure elements 20 alternately move into tight gripping engagement with the outer portion of the stone. This tight gripping engagement biases the stone inwardly into a tighter captured relationship within the fixed flexure elements 20.

With the stone thus tightly engaged, the canula assembly 12 can be withdrawn from the patient outwardly of the installed percutaneous tract. Note that during this fixed withdrawing movement the broader fixed flexure elements 20 are leading.

Referring now more particularly to FIGS. 7–9, it will be understood that the medical extractor 10 and the gripping and releasing mechanism 22 used therein can be modified to enable the extractor to be used nephroureteroscopically. FIGS. 7, 8 and 9 illustrate a modified canula assembly, generally indicated at 112, which has been miniaturized for urinary tract travel and is capable of being substituted in the device 10 for the canula assembly 12 heretofore described.

The canula assembly 112 is essentially constructed as an elongated wall structure providing a generally smooth exterior periphery and a hollow interior. In the embodiment shown, the elongated wall structure is formed by three coextensive side-by-side flexible tubular members, generally indicated at 116, disposed in an annular array. The tubular members 116 are formed of a suitable plastic material such as polyethylene, polypropylene, polyester, polyvinyl chloride, polyimide or the like. For the nephroureteroscopic application shown, the three tubular members 116 are fused together from the proximal ends thereof up to a confined position, indicated at 118 in FIGS. 7–9, spaced from the distal ends thereof.

At the distal end of the canula assembly 112, the flexible tubular members 116 extend outwardly of the confined position 118. The outwardly extending distal end sections of the flexible tubular members 116 constitute longitudinally fixed flexure elements 120 forming a part of an annularly expanding and retracting gripping and releasing mechanism, generally indicated at 122, constructed in accordance with the principles of the present invention at the distal end of the canula assembly 112.

The canula assembly 112 also includes three wires or rodular members, generally indicated at 124. The wires 124 are preferably made of stainless steel although other materials both electrically conducting and otherwise may be used. Each wire 124 has a length in excess of twice the length of the flexible tubular members 116. As shown, each wire 124 is bent at a midportion thereof so as to define a fixed wire section 126 and a movable wire section 128.

The three fixed wire sections 126 extend within the three flexible tubular members 116 with the bend being disposed in a flexure position on the longitudinally fixed flexure elements 120 which, as shown, is at the distal free ends of the tubular members 116. The three fixed wire sections 126 are fixed with respect to the three tubular members 116 within which they extend in a manner hereinafter to be more fully explained.

The three movable wire sections 128 also extend within the three tubular members 116, however, not within the same tubular members 116 as the fixed sections 126; but, instead, in adjacent tubular members 116. Each movable wire section 128 extends from the bend which connects it to the associated fixed wire section 126 through its associated tubular member 116 and outwardly beyond the proximal end thereof.

The canula assembly 112 is connected with the moving assembly 14 in the same manner as the canula assembly 12. The expanding and retracting mechanism 122 is moved between retracted insertion and extended maximum deployed positions by the moving assembly 14 in the same manner as previously described. The difference in operation lies in the manner of gaining access to the kidney area.

It is noted that the construction of the canula assembly 112 lends itself to miniaturization and flexibility, both qualities required to enable the distal end of the canula assembly 112 containing the gripping and releasing mechanism 122 to reach the kidneys through the urinary tract. Once the kidney area has been reached, the operation is the same as previously described.

Referring now more particularly to FIGS. 10 and 11 of the drawings, there is shown therein a modification of the medical extractor 10 and gripping and releasing mechanism 22 embodied therein which renders the extractor particularly useful in a ureteroscopic stone extraction procedure. FIGS. 10 and 11 illustrate a modified elongated canula assembly, generally indicated at 212, which can be used instead of the canula assembly 212 with the moving assembly 214.

The canula assembly 212 is essentially constructed as an elongated wall structure providing a generally smooth exterior periphery and a hollow interior. In the embodiment shown, the elongated wall structure is formed by a single flexible tubular member, generally indicated at 216. The tubular member 216 is formed of a suitable plastic material such as polyethylene, polypropylene, polyester, polyvinyl chloride, polyimide or the like.

At the distal end of the canula assembly 212 as indicated at 218, the flexible tubular member 216 fixedly receives end sections of four longitudinally fixed flexure elements 220 forming a part of an annularly expanding and retracting gripping and releasing mechanism, generally indicated at 222, constructed in accordance with the teachings of the present invention, at the distal end of the canula assembly 212.

The canula assembly 212 also includes four wires or rodular members, generally indicated at 224. The wires 224 are preferably made of stainless steel, although other materials both electrically conducting and otherwise may be used. As shown, each wire 224 is bent at a position spaced from one end a distance slightly greater than the length of the fixed flexure elements 220 so as to define a relatively short fixed wire section 226 and a relatively long movable wire section 228 having a length greater than the tubular member 216.

The four fixed wire sections 226 extend within the four fixed flexure elements 220 with the bend being disposed in a flexure position on the longitudinally fixed flexure elements 220 which, as shown, is at the distal free ends thereof. The free end portions of the four fixed wire sections 226 extend through the four fixed flexure elements 220 and are bent back over the outer peripheries of the associated four flexure elements 220 to an extent necessary to secure them between the interior periphery of the tubular member 216 and the coextensive exterior peripheries of the four fixed flexure elements which are likewise secured at the position of confinement 218.

The four movable wire sections 228 also extend within the four fixed flexure elements 220, however, not within the same fixed flexible element 220 as the fixed sections 226; but, instead, in adjacent fixed flexible elements 220 and through the tubular member 216 and outwardly beyond the proximal end thereof.

The canula assembly 212 is connected with the moving assembly 14 in the same manner as the canula assembly 12 except that only the proximal end of the single tubular member 218 is fixed between the frustoconical surfaces 40 and 44. The gripping and releasing mechanism 222 is moved between retracted insertion and extended maximum deployed positions by the moving assembly 14 in the same manner as previously described.

The extractor 10 with the canula assembly 212 is used in a ureteroscopic stone retrieval procedure, after the scope has been extended through the urinary tract and encountered a stone. The canula assembly 212 is then advanced through the scope to the region of the stone with the gripping and releasing mechanism 222 of the present invention in its retracted insertion position. The advance continues until the distal tip of the gripping and releasing mechanism 222 extends along the wall of the ureter beyond the stone. Thereafter, the gripping and releasing mechanism 222 is deployed in the manner previously described. After deployment, the stone is engaged by moving the deployed mechanism 222 rearwardly with the movable flexure element 264 between the ureteral wall and the stone, thus positioning the stone in the radially outwardly flexible fixed flexure elements 220. Once the stone is engaged, it is secured in the manner previously described.

It can be seen that the manner of utilizing the canula assembly 212 is generally similar to the manner in which conventional wire baskets are utilized. However, the open forward end and active expansion of the present gripping and releasing mechanism 222 allows the operator to disengage from a stone after the stone has been captured. This desirable function, which is lacking in conventional wire baskets, can become important to prevent certain surgical complications; such as ureter avulsion or retained basket. Moreover, the characteristics of the present gripping and releasing mechanism 222 which achieves the function also renders the extractor 210 more suitable to extracting impacted ureteral meatal stones because of the lack of an end plug such as is embodied in conventional baskets. Indeed, the extractor 210 of the present invention can be used in lieu of conventional wire baskets in all indications in addition to its use in lieu of conventional graspers. When used as either a grasper or a basket, an active expansion is provided which is not available in either conventional baskets or graspers.

It is important to note that the gripping and releasing mechanism 22 (or 122 or 222) of the present invention provides both active expansion and active retraction. That is, both expansion and retraction are actively under the control of the physical movement of structural wires. This active expansion is in contrast with expansion which takes place by virtue of metal memory or retraction which ends with a collapsed balloon. The intensity and extent of expansion can be varied by the selection of materials of the flexure elements 20 (or 120 or 220) and 64 (or 164 or 264), the selected diameter sizes and length of the fixed flexure elements 20 (or 120 or 220) and the selected diameter sizes and length of movement of the movable flexure elements 64 (or 164 or 264). The fixed flexure elements 20 (or 120 or 220) could be formed of a helically wound wire section with the movable wire section being either integral therewith or spot-welded thereto as disclosed in related application Ser. No. 09/069, 159, filed concurrently herewith, the disclosure of which is hereby incorporated by reference into the present specification. The essential characteristic is that each movable flexure element 64 (or 164 or 264) is transversely contained between the confined fixed position and the flexure position of the associated fixed flexure element 20 (or 120 or 220) in the sense of preventing the movable flexure element 64 (or 164 or 264) from bulging transversely outwardly in any direction to an extent sufficient to effect its proper arcuately outward flexure during operation.

The exact configuration of the gripping and releasing mechanism 22 (or 122 or 222) when in its maximum expanded deployed position will depend upon the relative flexure characteristics of the fixed flexure elements 20 (or 120 or 220) with respect to the movable flexure elements 64 (or 164 or 264). Where the movable flexure elements flex more readily than the fixed flexure elements, the latter tend to remain with their free ends displaced only radially outwardly as is the case with the fixed flexure elements 120 and movable flexure elements 164 in the canula assembly 1122 of FIGS. 7–9. In this case, the movable flexure elements do not have much tendency to move the free ends of the fixed flexure elements in an annular direction in addition to the radially outward direction. However, as the relative flexure characteristics are changed to a relationship in which the fixed flexure elements are more readily flexed than the movable flexure elements, the movement of the fixed flexure elements become more influenced by the flexure characteristics of the movable flexure elements. In this case, the free ends of the fixed flexure elements will have a significant annular movement in addition to their radially outward movement when reaching the maximum expanded deployed position as is the case with the canula assemblies 12 and 212 of FIG. 1–6 and 10–11. The result is that the fixed flexure elements each assume a more or less spiral configuration.

It will be understood that the terms "fixed" and "movable" used to identify the two different flexure elements 20 (or 120 or 220) and 64 (or 164 or 264) are used in the relative sense. That is, while the moving assembly 14 is operable to move the movable flexure elements 64 (or 164 or 264) with respect to the main body 30 of the moving assembly 14 and the fixed flexure elements 20 (or 120 or 220), it is within the contemplation of the present invention to utilize a conventionally known moving assembly in which the fixed flexure elements 20 (or 120 or 220) are moved with respect to the main body of the moving assembly 14 and the movable flexure elements 64 (or 164 or 264). In this case, the movable flexure elements 64 (or 164 or 264) still have relative movement with respect to the tubular canula structure 12 (or 112 or 212) and the fixed flexure elements 20 (or 120 or 220) are still fixed with respect to the tubular canula structure 12 (or 112 or 212). It is in this latter relative sense that the terms are used.

Figure 13:
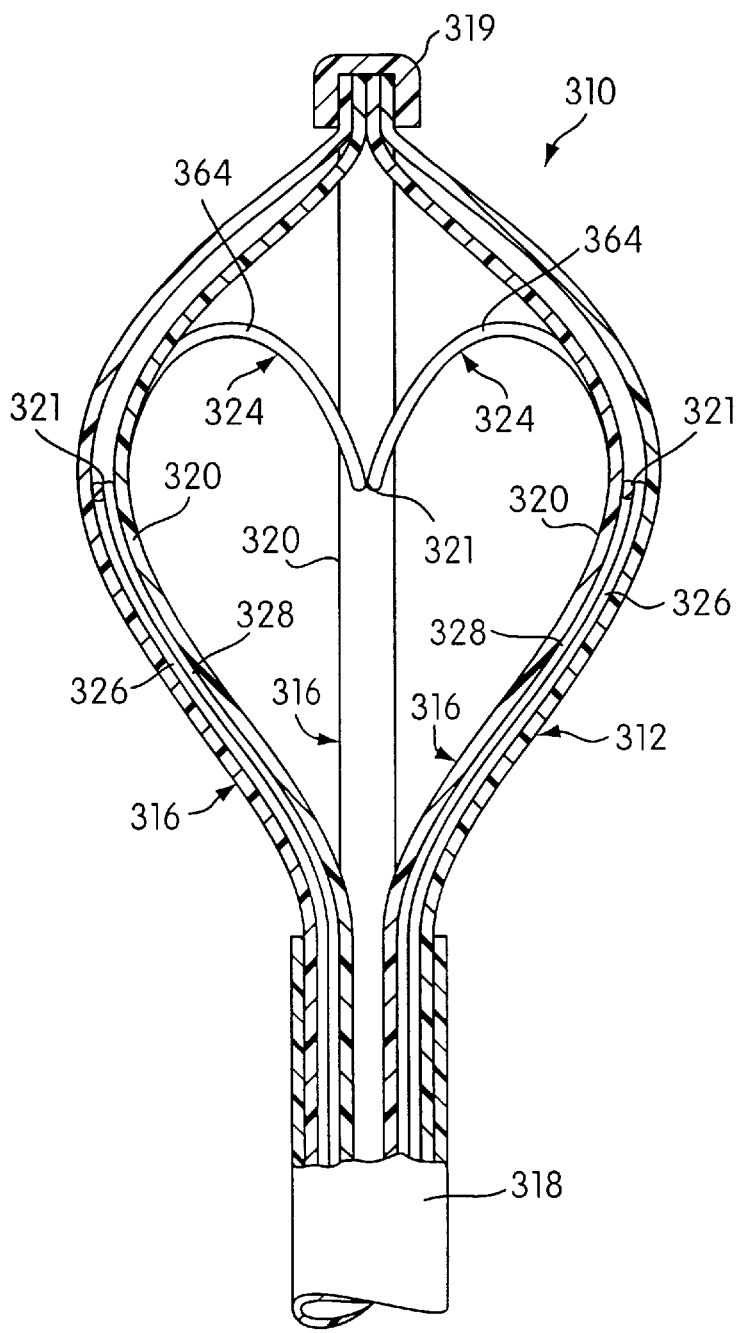
FIG. 13 is a view similar to FIG. 12, showing the gripping and releasing mechanism in an expanded maximum deployed position.

Referring now more particularly to FIGS. 12 and 13 of the drawings, there is shown therein an annularly expanding gripping and releasing mechanism, generally indicated at 322, which embodies the principles of the present invention, incorporated in a medical extractor, generally indicated at 310. The extractor 310 shown is particularly constructed to be used in an object extracting procedure in a ureter or other tubular body part, such as a bronchus track, blood vessel, or bronchus or bowel, where the object being extracted is, for example, a stone, a polyp, a foreign body, or vessel plaque. The medical extractor 310 includes, in general, an elongated canula assembly, generally indicated at 312, and a moving assembly, such as the moving assembly 14 previously described, operatively connected with the proximal end portion of the canula assembly 312.

The canula assembly 312 is essentially constructed as an elongated wall structure providing a generally smooth exterior periphery and a hollow interior. In the embodiment shown, the elongated wall structure is formed by four coextensive side-by-side flexible tubular members, generally indicated at 316. The tubular members 316 are formed of a suitable plastic material such as polyethylene, polypropylene, polyester, polyvinyl chloride or the like. For the object retrieval application shown, the four tubular members 316 are encased within an outer tubular member 318.

At the distal end of the canula assembly 312, the flexible tubular members 316 extend outwardly of the distal end of the outer tubular member 318. The outwardly extending distal end portions of the flexible tubular members 316 are fixed together by any suitable means such as an end cap 319. The distal portions of the flexible tubular members 316 extending from the distal end of the outer tubular members 318 to the end cap 319 constitute longitudinally fixed flexure elements 320 forming a part of the annularly expanding and retracting gripping and releasing mechanism, generally indicated at 322, constructed in accordance with the principles of the present invention, at the distal end of the canula assembly 312.

The canula assembly 312 also includes four wire or rodular members, generally indicated at 324. The wires 324 are preferably made of stainless steel. Each wire 324 has a length in excess of twice the length of the flexible tubular members 316. As shown, each wire 324 is bent at a midportion thereof so as to define a fixed wire section 326 and a movable wire section 328.

The four fixed wire sections 326 extend within the four flexible tubular members 316 with the bend being disposed in a flexure position on the longitudinally fixed flexure elements 322 which, as shown, is slightly outwardly of a midpoint thereon where each fixed flexure element 320 is formed with a transverse opening 321 in its wall. The four fixed wire sections 326 are fixed with respect to the four tubular members 316 within which they extend in a manner hereinafter to be more fully explained.

The four movable wire sections 328 also extend within the four tubular members 316, however, not within the same tubular members 316 as the fixed sections 326; but, instead, in adjacent tubular members 316. Each movable wire section 328 extends from the bend which connects it to the associated fixed wire sections 326 through the opening 321 of its associated tubular members 316 and outwardly beyond the proximal end thereof.

It will be understood that the distal ends of the outer tubular member 318, fixed wire sections 324 and flexible tubular members are fixed to the body of the moving assembly, as before, and the distal ends of the movable wire sections 326 are fixed, as before, to the moving member of the moving assembly.

In the use of the medical extractor 310 in a ureteral stone removal procedure, a ureteral scope is passed up to the obstructing stone. Next, the canula assembly 312 is inserted through the working channel of the scope into the ureter with the gripping and releasing mechanism 322 of the present invention in a retracted insertion position until the gripping and releasing mechanism 322 is alongside the stone to be retrieved. The optimal position of the gripping and releasing mechanism 322 in relation to the stone is that the portions of the fixed flexure elements 320 rearwardly of the transverse openings 321 therein are alongside the stone. As soon as the gripping and releasing mechanism 322 reaches the desired position as determined by visual inspection of the scope, the operator moves the moving member of the moving assembly forwardly away from the insertion position thereof toward the deployed position thereof.

As this movement takes place, the proximal ends of the movable wire sections 328 are moved. Since the movable wire sections 328 are captured peripherally throughout their extent, the movement of their proximal ends with the moving member of the moving assembly causes their opposite distal ends to move outwardly of the openings 321 in the flexible tubular members 316. Since the distal ends of each movable wire section 328 is fixed to the adjacent flexible tubular member 316 by virtue of the fixture of the integral fixed wire section 326 therewith, the movement of the distal end portions of the movable wire sections 328 outwardly of the tubular members 316 which contain them causes the fixed flexure elements 320 to be flexed radially outwardly at their midportions and the outwardly extending end sections of the movable flexure sections 328 to flex arcuately outwardly beyond the openings 321 of the fixed flexure elements 320.

At the end of this movement, the outwardly extending distal end portions of the movable wire sections 328, which constitute longitudinally movable flexure elements 364, are in arcuate configurations outwardly of the flexure positions of the fixed flexure elements 320, as shown in FIG. 13. It can be seen that the flexure position of each fixed flexure element 320 is biased outwardly by two associated movable flexure elements 364, one of which is integrally connected with the fixed wire section 326 therein and one of which is integral with the movable wire section 328 therein. Since the two movable flexure elements 364 associated with each fixed flexure element 320 have their opposite ends associated with the two adjacent fixed flexure elements 320, the flexural movement is imposed symmetrically upon each fixed flexure element 320 by the associated movable flexure elements 364. The result is that the gripping and releasing mechanism 322 expands from its retracted insertion position, as shown in FIG. 12, symmetrically both radially outwardly and longitudinally outwardly. In its expanded deployed position, as shown in FIG. 13, the gripping mechanism 322 is defined by four longitudinally outwardly arcuately flexed movable flexure elements 364 extending in an annular series or array. The expanded deployed gripping mechanism 322 is defined by four radially outwardly flexed fixed flexure elements 320 extending from a position of confinement determined by the position of the distal free end of the outer tubular member 318 to a longitudinally spaced position of confinement determined by the end cap 319.

As the gripping 322 is expanded with the stone in a predetermined position, the fixed flexure elements 320 move over and around the stone within the confines of the ureter causing the stone to lie within the expanded fixed flexure elements.

Once the stone is positioned within the expanded gripping and releasing mechanism 322, the operator simply moves the moving member of the moving assembly rearwardly away from the deployed position toward the insertion position. This rearward movement effectively retracts the movable flexure elements 364 back into the fixed flexure elements 320 of the gripping and releasing mechanism 322. As this movement progresses, the arcuate extent of the movable flexure elements 364 becomes smaller and the flexure positions at the midportions of the fixed flexure elements 320 move radially inwardly. As the movable flexure elements 364 continue to move within the fixed flexure elements 320, the outer portion of the gripping and releasing mechanism 322 is retracted both radially and longitudinally inwardly. The retracting outer portion of the gripping and releasing mechanism 322 including the movable flexure elements 364 and midportions of the fixed flexure elements 320 alternately move into tight gripping engagement with the outer portion of the stone.

With the object thus tightly engaged, the canula assembly 312 can be withdrawn from the patient outwardly of the ureter into which it was inserted. Note that during this fixed withdrawing movement the broader fixed flexure elements 320 are leading. It can be seen that the device 310 is capable of operating in any situation where conventional basket devices have been used in the past.

The disclosed manner of securing the ends of the movable flexure elements 364 to the fixed flexure elements 320 is desirable in that it is economical and accommodates miniaturization very well. Other well-known modes of securement may be used especially when larger annular sizes can be used. For example, where the fixed flexure elements 320 are molded rather than being assembled from extruded tubing, the wire ends can be embedded therein as inserts in the mold.

It is important to note that the gripping and releasing mechanism 322 of the present invention provides both active expansion and active retraction in the same manner as before.

Referring now more particularly to FIGS. 14–15 of the drawings, there is shown therein an annularly expanding and retracting mechanism, generally indicated at 422, constructed in accordance with the principles of the present invention, embodied in a medical coagulating, cutting and extracting device, generally indicated at 410. The device 410 shown is particularly constructed to be used in a gastrointestinal polyp removal procedure in conjunction with a Bovie electrical pad of conventional construction to enable the device to effect a coagulating and cutting action in accordance with Bovie electrical technology to utilize a Bovie grounding pad and a Bovie electrical circuit assembly. The medical coagulating, cutting and retrieving device 410 includes, in general, an elongated canula assembly, generally indicated at 412, and a moving assembly, generally indicated at 414, operatively connected with the proximal end portion of the canula assembly 412. The gripping and releasing mechanism 422 embodied in the distal end of the canula assembly 412 and serves to perform the cutting and coagulating functions in addition to the gripping function enabling the extraction to be effected.

The canula assembly 412 is essentially constructed as an elongated wall structure providing a generally smooth exterior periphery and a hollow interior. In the embodiment shown, the elongated wall structure is formed by four coextensive side-by-side flexible tubular members, generally indicated at 416. The tubular members 416 are formed of a suitable plastic material such as polyethylene, polypropylene, polyester, polyvinyl chloride or the like. For the polyp removal application shown, the four tubular members 416 are encased within a thin walled outer tubular member 418.

At the distal end of the canula assembly 412, the flexible tubular members 416 extend outwardly of the distal end of the outer tubular member 418. The outwardly extending distal end portions of the flexible tubular members 416 constitute longitudinally fixed flexure elements 420 forming a part of the gripping and releasing mechanism 422 at the distal end of the canula assembly 412.

The canula assembly 412 also includes four wires or rodular members, generally indicated at 424. The wires 424 are preferably made of stainless steel. Each wire 424 has a length in excess of twice the length of the flexible tubular members 416. As shown, each wire 424 is bent at a midportion thereof so as to define a fixed wire section 426 and a movable wire section 428.

The four fixed wire sections 426 extend within the four flexible tubular members 416 with the bend being disposed in a flexure position on the longitudinally fixed flexure elements 420 which, as shown, is at the distal free ends of the tubular members 416. The four fixed wire sections 426 are fixed with respect to the four tubular members 416 within which they extend in a manner hereinafter to be more fully explained.

The four movable wire sections 428 also extend within the four tubular members 416, however, not within the same tubular members 416 as the fixed sections 426; but, instead, in adjacent tubular members 416. Each movable wire section 428 extends from the bend which connects it to the associated fixed wire section 426 through its associated tubular member 416 and outwardly beyond the proximal end thereof.

The preferred embodiment of the moving assembly 414 shown in FIGS. 16–19 includes a main body, generally indicated at 430, molded of a suitable plastic material. The main body 430 is of generally tubular construction and of a size to be conveniently gripped in one hand. The main body 430 is formed of a peripheral wall 432 having an end wall 434 closing a forward end thereof. The rearward end of the peripheral wall 432 is open and exteriorly threaded, as indicated at 436. An elongated slot 438 is formed in the peripheral wall 432 which extends rearwardly from the forward end wall 434 thereof completely through the rear end thereof.

The forward end wall 434 is formed with a central opening, generally indicated at 440. The opening 440 includes a forward portion 442 which is shaped to receive therethrough the four flexible tubular members 416. The forward end wall 434 has its forward extremity shaped into a frusto-conical exterior surface 444 and an intermediate portion of reduced diameter is formed with exterior threads as indicated at 446. The exterior frusto-conical surface 444 is sized to cooperate with an interior frusto-conical surface 448 formed on a mounting element 450, in the form of an interiorly threaded cap. The cap mounting element 450 is centrally apertured to receive therethrough the outer tubular member 418 so as to be capable of being initially moved over the proximal end of the outer tubular member 418. The cap mounting element 450 when threaded on the threads 446 of the end wall 434 serves to secure the proximal end of the outer tubular member 418 to the main body 430 of the moving assembly 414.

It will be understood, that the securement can be effected by splitting the proximal end of the outer tubular member 418 and spreading the split end over the exterior frusto-conical surface 440. As the cap mounting element 450 is thereafter turned on the threads 446, the split proximal end of the outer tubular member 418 will be squeezed between the exterior and interior frusto-conical surfaces 444 and 448 until securely held therebetween.

As best shown in FIG. 16, the central opening 440 in the forward end wall portion 434 at its rearward portion is in the form of a small central opening 452 having four separate cylindrical openings 454 spaced annularly thereabout. Each separate opening 454 is of a size to receive therethrough one of the four tubular members 416. The central opening 440 includes an intermediate transitional portion which includes four radially inwardly opening inclined grooves 456 shaped to receive the four tubular members 416 therein and direct them rearwardly and radially outwardly from the forward opening portion 442 to the four separate rearward openings 454.

The portion of each tubular member 416 which faces radially inwardly at a position just forwardly of the rearward opening 454 through which it extends is apertured to enable the fixed wire section 426 therein to be led outwardly through the aperture and rearwardly through the small central opening 452 in the forward end wall 434. The four proximal end portions of the four fixed wire sections 428 extend rearwardly through a cylindrical through bore 458 formed centrally within a moving member, generally indicated at 460.

The moving member 460 has its exterior shaped into a generally cylindrical configuration so as to slidably engage within the interior of the peripheral wall 432. The moving member 460 moves within the main body 430 in opposite longitudinal directions between an insertion position, as shown in FIG. 17 and a maximum expanded position. The moving member 460 includes an upstanding digitally engageable portion 462 which extends upwardly through the slot 438 in the peripheral wall 432. The digitally engageable portion 462 includes a projection 464 at its forward end for facilitating the digital movement of the moving member 460 in both longitudinal directions with respect to the main body 430.

The proximal end portions of the four tubular members 416 with the movable wire sections 428 therein extend rearwardly of the separate openings 454 in the forward end wall 434 and are slidably received within four annularly spaced cylindrical counterbores 466 formed in the moving member 460 forwardly of four rearward throughbores 468. The counterbores 466 are sized to slidably receive the proximal end portions of the tubular members 416 and the throughbores 468 are sized to receive therethrough the proximal end portions of the movable wire sections 428 which extend rearwardly from the rear extremities of the tubular members 416.

The rear end portion of the moving member 460 is formed with a frusto-conical exterior surface 470 over which the terminal ends of the movable wire sections 428 are bent when the movable member 460 is disposed in its insertion position. A mounting element 472 having a mating interior frusto-conical surface 474 is engaged with the end of the moving member 460 to capture the bent over terminal ends of the movable wire sections 428 between the exterior and interior frusto-conical surfaces 470 and 474. The mounting element 472 is retained in pressure tight engagement with the movable member by a nut 476 threaded on a central rearward projection 478 on the moving member 460.

An end cap 480 is threadedly mounted on the exterior threads 436 at the rear end of the main body 430. The end cap 480 includes an interior forwardly projecting annular portion which enters within the interior rear end of the peripheral wall 432 to maintain the diametrical integrity of the peripheral wall 432. The end cap 480 is centrally apertured to receive the terminal ends of the four fixed wire sections 426 extending through the throughbore 450 of the movable member 452. The terminal ends of the four fixed wire sections 426 are fixed at the end cap and electrically connected with a lead wire 482.

The device 410 is used in an exemplary intestinal polyp removing procedure of the type which heretofore utilized a colonoscope and a polypectomy snare and a Bovie type pad and electrical circuitry assembly. Basically, the device 410 is utilized in lieu of the polypectomy snare. The use of the device occurs after the passed scope has enabled the physician to visualize the polyp. Prior to usage, the gripping and releasing mechanism 422 and the moving member 460 of the moving assembly 414 are disposed in the insertion positions thereof as shown in FIGS. 14 and 16. The distal end of the canula assembly 412 is then inserted through the working channel of the scope to the area of the polyp. The physician then manually moves the movable member 460 forwardly to deploy or expand the gripping and releasing mechanism 422.

When the moving member 452 reaches the deployed position, as shown in FIG. 17, the outwardly extending distal end portions of the movable wire sections 428, which constitute longitudinally movable flexure elements 484, are in arcuate configurations outwardly of the flexure positions of the fixed flexure elements 420, as shown in FIG. 15. It can be seen that the flexure position of each fixed flexure element 420 is biased outwardly by two associated movable flexure elements 464, one of which is integrally connected with the fixed wire section 426 therein and one of which is integral with the movable wire section 428 therein. Since the two movable flexure elements 484 associated with each fixed flexure element 420 have their opposite ends associated with the two adjacent fixed flexure elements 420, the flexural movement is imposed symmetrically upon each fixed flexure element 420 by the associated movable flexure elements 484. The result is that the gripping and releasing mechanism 422 expands from its retracted insertion position, as shown in FIG. 14, both radially outwardly and longitudinally outwardly. In its maximum expanded deployed position, as shown in FIG. 15, the gripping and releasing mechanism 422, as before, is defined at its outer portion by four longitudinally outwardly arcuately flexed movable flexure elements 464 extending in an open annular series or array. The inner portion of the maximally expanded deployed gripping and releasing mechanism 422 is defined by four radially outwardly flexed fixed flexure elements 420 extending from a position of confinement determined by the position of the distal free end of the outer tubular member 418.

The deployment configuration whether maximal or less enables the operator to move the expanded gripping and releasing mechanism 422 longitudinally over the targeted polyp until the deployed movable flexure elements 484 are positioned near the base of the stalk of the targeted polyp. The physician then moves the moving member 460 rearwardly to retract the gripping and releasing assembly 422 until the movable flexure elements 484 are in contact with the outer periphery of the base of the stalk of the polyp.

With the device 410 in this condition, after the grounding pad has been positioned over a large muscle mass on the skin of the patient, the electrical circuit assembly is operated to generate a coagulating current penetrating from the energized movable flexure elements 384 into the base of the stalk of the polyp to the grounding pad. Thereafter, the electrical circuit assembly is operated to generate a cutting current penetrating from the energized movable flexure elements 384 to the grounding pad. The cutting action enables the physician to contract the gripping and releasing mechanism 422 by moving the moving member 460 rearwardly. This sequence of establishing first a coagulating current then a cutting current and then further contracting the movable flexure elements 384 is continued until the stalk of the polyp has been transected. The final sequence results in the polyp being gripped within the fixed flexure elements 320, thus entrapping the polyp in the contracted gripping and releasing mechanism 422. Thereafter, the physician withdraws the device 410 with the entrapped polyp and the scope.

The advantages of utilizing the device 410 in lieu of a conventional snare are that the deployment of the gripping and releasing mechanism 422 moves the movable flexure elements 384 into an arcuate outwardly flexed configuration which enables it to be positioned at the base of the stalk of the polyp and maintained there as the sequence progresses. The closer to the base the polyp can be transected maximizes the possibility of complete removal. In addition, the device 410 provides automatic entrapment so that separate retrieval of the transected polyp is not required.

Referring now more particularly to FIGS. 20–26 of the drawings, there is shown therein a two pole medical coagulating, cutting and retrieving device, generally indicated at 510, which embodies an annularly expanding and retracting gripping and releasing mechanism, generally indicated at 522, constructed in accordance with the principles of the present invention. The embodiment shown is particularly constructed to be used in a gastro-intestinal polyp removal procedure. The two pole medical coagulating, cutting and retrieving device 510 includes, in general, an elongated canula assembly, generally indicated at 512, and a moving assembly, generally indicated at 514, operatively connected with the proximal end portion of the canula assembly 512.

The canula assembly 512 is essentially constructed as an elongated wall structure providing a generally smooth exterior periphery and a hollow interior. In the embodiment shown, the elongated wall structure is formed by four coextensive side-by-side flexible bi-tubular members, generally indicated at 516. The bi-tubular members 516 are formed of a suitable plastic material such as polyethylene, polypropylene, polyester, polyvinyl chloride or the like. For the two pole polyp removal application shown, the four bi-tubular members 516 each consist of a pair of side-by-side tubular members 517 and 518 integrally interconnected at their exterior peripheries. The four bi-tubular members 516 are fused together throughout substantially their entire length so that each tubular member 517 is fused to the tubular member 518 of the adjacent bi-tubular member 516 so as to form an annular array of alternating tubular members 517 and 518 as shown in FIG. 23.

At the distal end of the canula assembly 512, the flexible bi-tubular members 516 extend unfused or separately outwardly from a confined position spaced from their free ends. The outwardly extending distal end portions of the flexible bi-tubular members 516 constitute longitudinally fixed flexure elements 520 forming a part of the annularly expanding and retracting gripping and releasing mechanism 522 at the distal end of the canula assembly 512.

The canula assembly 512 also includes four wires or rodular members, generally indicated at 524. The wires 524 are preferably made of stainless steel. Each wire 524 has a length in excess of twice the length of the flexible bi-tubular members 516. As shown, each wire 524 is bent at a mid-portion thereof so as to define a fixed wire section 526 and a movable wire section 528.

The four fixed wire sections 526 extend within the four tubular members 517 with the bend being disposed in a flexure position on the longitudinally fixed flexure elements 520 which, as shown, is at the distal free ends of the bi-tubular members 516. The four fixed wire sections 526 are fixed with respect to the four tubular members 517 within which they extend in a manner hereinafter to be more fully explained.

The four movable wire sections 528 extend within the four tubular members 518. Each movable wire section 528 extends within the tubular member 518 which is fused to the tubular member 517 within which the associated fixed wire section 526 extends. In this way, the outward movement of each movable wire section 528 can have the effect of separating the fixed flexure element 520 in which it moves from the adjacent fixed flexure element 520 within which the associated fixed wire section 526 extends in fixed relation. It will also be noted that a small dividing wall 529 extends upwardly from the juncture of the tubular member 517 and 518 of each bi-tubular member 516. The walls 529 serve to electrically insulate the fixed and movable wire sections 526 and 128 associated with each bi-tubular member 516.

The preferred embodiment of the moving assembly 514 shown in FIGS. 23–28 includes a main body, generally indicated at 530, molded of a suitable plastic material. The main body 530 is of generally tubular construction and of a size to be conveniently gripped in one hand. The main body 530 is formed of a peripheral wall 532 having an end wall 534 closing a forward end thereof. The rearward end of the peripheral wall 532 is of reduced diameter and exteriorly threaded, as indicated at 536. An elongated slot 538 is formed in the peripheral wall 532 which extends rearwardly from the forward end wall 534 thereof completely through the rear end thereof.

The forward end wall 534 is formed with a series of four cylindrical openings 540 extending axially therethrough in annularly spaced relation about the axis thereof. The four openings 540 are positioned to receive the proximal ends of the four tubular members 518. The four tubular members 517 are terminated at the forward end of the forward end wall 534. However, the fixed wire sections 526 therein extend outwardly therefrom a short distance.

The forward end wall 534 has its forward extremity outwardly of the openings 540 shaped into a frusto-conical exterior surface 542 and an intermediate portion of reduced diameter is formed with exterior threads as indicated at 544. The exterior frusto-conical surface 542 is sized to cooperate with an interior frusto-conical surface 546 formed on a mounting element 548. The mounting element 548 is held in place by an interiorly threaded cap 550. Both the mounting element 548 and the cap 550 are centrally apertured to receive therethrough the array of bi-tubular members 516 so as to be capable of being initially moved over the proximal end thereof. The cap 550 when threaded on the threads 544 of the end wall 534 serves to secure the outwardly extending ends of the fixed wire sections 526 and the proximal ends of the tubular member 517 to the main body 530 of the moving assembly 414.

It will be understood, that the securement can be effected by cutting the proximal ends of the outer tubular member 517 to form outer tabs and spreading the tabs over the exterior frusto-conical surface 542 so that the outwardly extending ends of the fixed wire sections 526 are presented to engage the exterior frusto-conical surface 542. Thereafter, the mounting element 548 can be moved in place and, finally, the cap 550. As the cap 550 is thereafter turned on the threads 544, the proximal ends of the fixed wire sections 526 and the cut tab ends of the tubular members 517 will be squeezed between the exterior and interior frusto-conical surfaces 542 and 546 until securely held therebetween.

Referring now more particularly to FIG. 27, it will be noted that two opposite fixed wire sections 526 have the outwardly extending proximal ends thereof pressed into engagement with two separate electrical conductors 552 and 554 each being in the form of an elongated thin narrow strip of conductive metal. As shown, the forward end of each electrical conductor strip 552 and 554 is bent inwardly to rest within a suitable receiving recess formed in the frusto-conical surface 542. The remainder of the two electrical conductor strips 552 and 554 extend within two grooves 556 and 558 respectively formed in the peripheral wall 532 of the main body 530 throughout the longitudinal extent thereof. The grooves 556 and 558 extend through the forward end wall 534 as rectangular openings and through the remainder of the peripheral wall 532 as T-shaped grooves which open radially inwardly.

The proximal end portions of the tubular members 518 extend through the cylindrical openings 540 in the forward end wall 532 rearwardly thereof. The movable wire sections therein extend rearwardly from the terminal ends of the tubular members 518 and are connected with a moving member, generally indicated at 560, in a manner hereinafter to be more fully explained.

The moving member 560 has its exterior shaped into a generally cylindrical configuration so as to slidably engage within the interior of the peripheral wall 532. The moving member 560 moves within the main body 530 in opposite longitudinal directions between an insertion position, as shown in FIG. 23 and a maximum expanded position. The moving member 560 includes an upstanding digitally engageable portion 562 which extends upwardly through the slot 538 in the peripheral wall 532. The digitally engageable portion 562 includes a projection 564 at its forward end for facilitating the digital movement of the movable member 560 in both longitudinal directions with respect to the main body 530.

The proximal end portions of the four tubular members 518 with the movable wire sections 528 therein extend rearwardly of the cylindrical openings 540 in the forward end wall 534 and are slidably received within four annularly spaced cylindrical counterbores 566 formed in the moving member 560 forwardly of four rearward throughbores 568. The counterbores 566 are sized to slidably receive the proximal end portions of the tubular members 518 and the throughbores 568 are sized to receive therethrough the proximal end portions of the movable wire sections 528 which extend rearwardly from the rear extremities of the tubular members 518.

The rear end portion of the moving member 560 is formed with a frusto-conical exterior surface 570 over which the terminal ends of the movable wire sections 528 are bent when the movable member 560 is disposed in its insertion position. A mounting element 572 having a mating interior frusto-conical surface 574 is engaged with the end of the moving member 560 to capture the bent over terminal ends of the movable wire sections 528 between the exterior and interior frusto-conical surfaces 570 and 574. The mounting element 572 is retained in pressure tight engagement with the moving member 560 by a nut 576 threaded on a central rearward projection 578 on the moving member 560.

As best shown in FIG. 28, it will be noted that two opposite movable wire sections 528 have their extremities pressed into engagement with two separate electrical contacts 580 and 582, each being in the form of a short thin narrow strip of conductive metal. As shown, an inner end portion of each electrical contact 580 and 582 is fitted within a suitable securing recess formed in the frusto-conical surface 570 of the moving member 560. The outer end portion of the electrical contacts 580 and 582 are bent outwardly into arcuate configurations so as to make electrical sliding contact with two separate electrical conductors 584 and 586 extending within two opposed grooves 588 and 590 formed in the rear end portion of the cylindrical wall 532. The conductors 584 and 586 and grooves 588 and 590 are similar in construction to the conductors 552 and 554 and grooves 556 and 558.

The end edge of the peripheral wall 532 is formed with two recesses for receiving a pair of arcuate projections formed on an end disk 592 which projects within the interior of the peripheral wall 532. Mounted on the exterior of the end disk 592 are four electrical contacts 594, 596, 598 and 600. The inner portions of the contacts 594, 596, 598 and 600 are fixed to the exterior surface of the end disk while the outer ends thereof are curved arcuately outwardly to make electrical contact with the rear ends of the electrical conductors 552, 554, 584 and 586 respectively.

Figure 21:
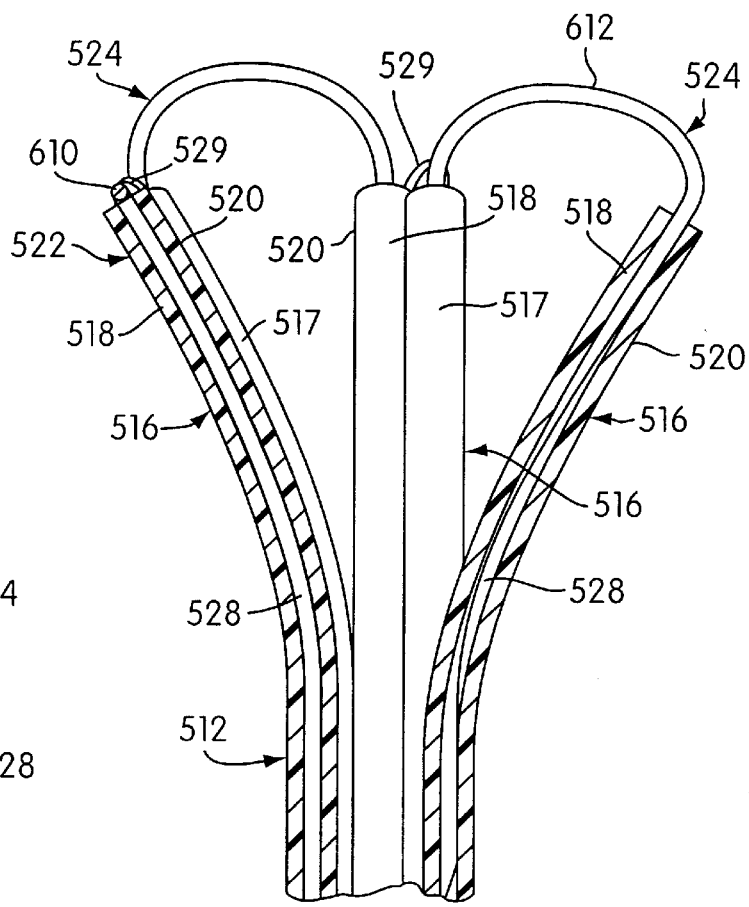
FIG. 21 is a view similar to FIG. 20, showing the gripping and releasing mechanism in a retracted insertion position.
Figure 20:
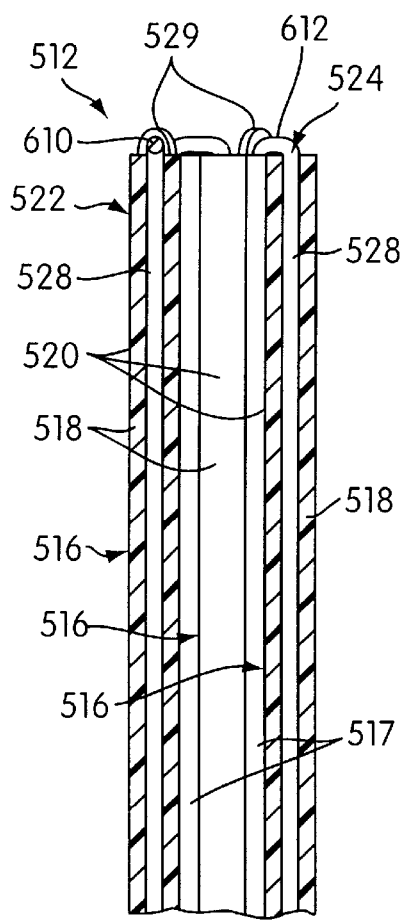
FIG. 20 is a vertical sectional view of another form of gripping and releasing mechanism constructed in accordance with the principles of the present invention embodied in the distal end portion of a canula assembly of another medical coagulating, cutting and retrieving device, showing the gripping and releasing mechanism in a retracted insertion position.

As best shown in FIG. 21, the contacts 594 and 598 are fixed to the end disk 592 by headed screw elements 602 which, in turn, secure two wires 604 which extend rearwardly to form one pole circuit in a suitable control wiring board (not shown). Correspondingly, the two contacts 596 and 600 are fixed to the end disk 592 by headed screw elements 606 which, in turn, secure two wires 608 which extend rearwardly to form a second pole circuit in the wiring board.

The end disk 592 is secured in the rear end of the peripheral wall by a threaded end cap 610 which is threadedly engaged on the exterior threads 536 of the peripheral wall 532. The end cap 610 is centrally apertured to receive the wires 604 and 608 rearwardly therethrough.

Figure 22:
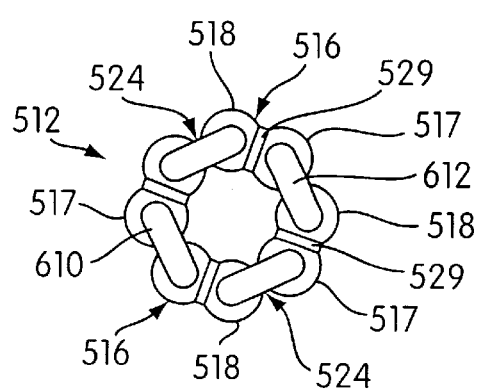
FIG. 22 is a top plan view of the distal end of the canula assembly shown in FIG. 10.

The device 510 is used in the same way as the device 410 except that the circuit for the coagulating current and the cutting current is contained within the device 510 and no external grounding pad is used. The circuit within the device includes two opposing poles in the form of two opposing movable wire sections 528. More particularly, it will be noted that the portion of each movable wire section 528 which extends from the flexible tubular member 517 to which it is fixed moves into and out of the adjacent fixed flexure elements. This portion of each movable wire section 528 constitutes a movable flexure element. The four movable flexure elements constitute basic components of the gripping and releasing mechanism 522. Consequently, the two poles comprise two opposed movable flexure elements which are designated 610 and 612 among the four provided as best shown in FIG. 22.

The circuit through the pole provided by the movable flexure element 610 consists of electrical contact 594, conductor strip 552, fixed wire section 526, movable flexure element 610 integral therewith, movable wire section 528 integral therewith, electrical contact 580, conductor strip 584, and electrical contact 598. This circuit is completed through lead wires 604. The circuit through the pole provided by the movable flexure element 612 consists of electrical contact 596, conductor strip 554, fixed wire section 526, movable flexure element 612 integral therewith, movable wire section 528 integral therewith, electrical contact 582, conductor strip 586 and electrical contact 600. This circuit is completed through lead wires 608. It will be noted that the sliding engagement of the contacts 580 and 582 with conductor strips 584 and 586 respectively enables the circuit to remain completed within the device 510 in any position of the movable member 560.

While the above-described uses of the annularly expanding and retracting gripping and releasing mechanism of the present invention are all with respect to medical devices, it will be understood that uses in other devices and combinations are contemplated. For example, the gripping and releasing mechanism has applicability to robotics especially in miniaturized robotics. Other presently contemplated usage is in toys where moving objects are required to be gripped and then released. Basically, the mechanism of the present invention is useful in any situation where it is desirable to provide a gripping and releasing action and particularly such an action provided by annular expansion and retraction.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An annularly expanding and retracting gripping and releasing mechanism comprising an annular series of longitudinally fixed flexure elements and a corresponding series of longitudinally movable flexure elements;

said fixed flexure elements being fixed relatively together in an annular array at a confining fixed position and having a flexure position spaced longitudinally outwardly therefrom;

each of said fixed flexure elements being constructed and arranged to flex at the flexure position thereof transversely outwardly and inwardly about the confined fixed position thereof;

each of said movable flexure elements having an end fixed with respect to the flexure position of one of said fixed flexure elements and extending therefrom in longitudinally movable and generally transversely confined relation to a receiving portion of an adjacent fixed flexure element the outer end of which is adjacent the flexure position thereof;

said movable flexure elements being constructed and arranged to be moved longitudinally in an outward direction with respect to the receiving portions associated therewith to extend in an arcuately flexed condition generally beyond the flexure positions of said fixed flexure elements to cause the latter to flex transversely outwardly and create an expanded condition defined by an annular series of transversely outwardly flexed fixed flexure elements interconnected by an annular series of arcuately flexed portions of said movable flexure elements;

said movable flexure elements being constructed and arranged to be moved when in said expanded condition in a direction inwardly with respect to the receiving portions associated therewith to cause said expanded condition to progressively retract during which the annular series of transversely outwardly flexed fixed flexure elements are progressively less flexed transversely outwardly and the annular series of arcuately flexed portions of said movable flexure elements have a progressively less arcuate extent.

2. An annularly expanding and retracting gripping and releasing mechanism as defined in claim 1 including an elongated tubular canula structure having a distal end fixedly connected with said series of fixed flexure elements, and a moving assembly including a body member fixed to a proximal end of said tubular canula structure and a moving member mounted on said body member for movement in one direction and in an opposite direction, an elongated motion transmitting canula structure within said tubular canula structure connected at a distal end with said movable flexible elements and at a proximal end with said moving member, said moving member and said motion transmitting canula structure being constructed and arranged so that movement of said moving member in the one direction creates said expanded condition of said flexure elements and movement of said moving member in the opposite direction causes the expanded condition of said flexure elements to progressively retract said motion-transmitting canula structure and certain of said movable flexure elements being constructed and arranged to be connected within an electrical circuit operable to pass an electrical current therethrough so that during a progressive retraction of said flexure elements from the expanded condition thereof electrical current passing through said movable flexure elements can be sequentially used to cut coagulate tissue around which the retraction of said flexure elements is taking place.

3. An annularly expanding and retracting gripping and releasing mechanism as defined in claim 2 wherein said fixed flexure elements are formed of plastic tubular members and said movable flexure elements are formed of wire sections, said tubular canula structure including plastic tubular members forming a continuation of the plastic tubular members forming said fixed flexure elements, said motion-transmitting canula structure including motion-transmitting wire sections forming continuations of the wire sections forming said movable flexure elements.

4. An annularly expanding and retracting gripping and releasing mechanism as defined in claim 3 wherein the wire sections forming said movable flexure elements have fixed wire sections forming continuations thereof, said fixed wire sections being fixed within said plastic tubular members.

5. An annularly expanding and retracting gripping and releasing mechanism as defined in claim 4 wherein there are four fixed flexure elements, each being formed of a plastic tubular member defining two parallel passages within which the motion transmitting wire section of the movable wire section thereof is mounted and within the other one of which the fixed wire section of the adjacent movable wire section is fixed.

6. An annularly expanding and retracting gripping and releasing mechanism as defined in claim 5 wherein opposite movable wire sections and the associated motion transmitting and fixed wire sections thereof are constructed and arranged to be connected within an electrical circuit operable to pass an electric current from one of said opposite movable wire sections through tissue surrounded by said flexure elements in an expanded condition to the other of said opposite movable wire sections so that during a progressive retraction of said flexure elements from the expanded condition thereof electrical current passing between said opposed movable wire sections can be sequentially used to cut and coagulate the tissue surrounded by said flexure elements.

7. An annularly expanding and retracting gripping and releasing mechanism as defined in claim 1 including an elongated tubular canula structure having a distal end fixedly connected with said series of fixed flexure elements and a moving assembly including a body member fixed to a proximal end of said tubular canula structure and a moving member mounted on said body member for movement in one direction and in an opposite direction, an elongated motion transmitting canula structure within said tubular canula structure connected at a distal end with said movable flexure elements and at a proximal end with said moving member, said moving member and said motion transmitting canula structure being constructed and arranged so that movement of said moving member in the one direction creates said expanded condition of said flexure elements and movement of said moving member in the opposite direction causes the expanded condition of said flexure elements to progressively retract, said fixed flexure elements being formed of plastic tubular members and said movable flexure element being formed of wire sections, said tubular canula structure including plastic tubular members forming a continuation of the plastic tubular members forming said fixed flexure elements, said motion transmitting canula structure including motion transmitting wire sections forming continuation of the wire sections forming said movable flexure elements, each movable wire section forming a movable flexure element extends from the continuing fixed wire section thereof through an opening in the central portion of the plastic tubular member within which the fixed wire section is fixed, said plastic tubular members having outer ends spaced form the openings thereof connected together.

8. An annularly expanding and retracting gripping and releasing mechanism as defined in claim 7 wherein the wire sections forming said movable flexure elements have fixed wire sections forming continuations thereof, said fixed wire sections being fixed within said plastic tubular members.

9. An annularly expanding and retracting gripping and releasing mechanism as defined in claim 1 wherein said fixed flexure elements are plastic tubular members.

10. An annularly expanding and retracting gripping and releasing mechanism as defined in claim 9 wherein said movable flexure elements are metal wire sections.

11. An annularly expanding and retracting gripping and releasing mechanism as defined in claim 10 wherein said metal wire sections are formed of stainless steel.

12. An annularly expanding and retracting gripping and releasing mechanism as defined in claim 1 wherein said movable flexure elements are metal wire sections.

13. An annularly expanding and retracting gripping and releasing mechanism as defined in claim 12 wherein said metal wire sections are formed of stainless steel.

* * * * *